(12) United States Patent
McKinley et al.

(10) Patent No.: US 7,776,094 B2
(45) Date of Patent: *Aug. 17, 2010

(54) SPINAL IMPLANTS AND METHODS FOR INSERTING SPINAL IMPLANTS INTO INTERVERTEBRAL SPACES

(75) Inventors: James T. McKinley, Woodside, CA (US); James Marino, La Jolla, CA (US); Corbett Stone, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 726 days.

This patent is subject to a terminal disclaimer.

(21) Appl. No.: 11/121,394

(22) Filed: May 3, 2005

(65) Prior Publication Data

US 2005/0216088 A1 Sep. 29, 2005

Related U.S. Application Data

(62) Division of application No. 10/032,121, filed on Dec. 21, 2001, now Pat. No. 6,887,248, which is a division of application No. 09/320,081, filed on May 26, 1999, now Pat. No. 6,368,325.

(60) Provisional application No. 60/120,663, filed on Feb. 19, 1999, provisional application No. 60/113,651, filed on Dec. 23, 1998, provisional application No. 60/086,945, filed on May 27, 1998.

(51) Int. Cl.
*A61F 2/44* (2006.01)
(52) U.S. Cl. .................. 623/17.16; 623/17.11; 128/898
(58) Field of Classification Search .................. 606/61, 606/246, 247, 250; 623/17.11–17.16; 128/898
See application file for complete search history.

(56) References Cited

U.S. PATENT DOCUMENTS

| | | | |
|---|---|---|---|
| 3,486,505 A | 12/1969 | Morrison | |
| 3,518,993 A | 7/1970 | Blake | |
| 3,604,487 A | 9/1971 | Gilbert | |
| 3,745,995 A | 7/1973 | Kraus | |
| 3,848,601 A | 11/1974 | Ma et al. | |
| 4,026,304 A * | 5/1977 | Levy ........................... | 607/51 |
| 4,026,305 A | 5/1977 | Brownlee et al. | |
| 4,646,738 A | 3/1987 | Trott | |
| 4,657,550 A | 4/1987 | Daher | |
| 4,743,256 A | 5/1988 | Brantigan | |
| 4,781,591 A | 11/1988 | Allen | |
| 4,834,757 A | 5/1989 | Brantigan | |

(Continued)

FOREIGN PATENT DOCUMENTS

CA 2015507 1/1999

(Continued)

OTHER PUBLICATIONS

Alleyne, Cargill H., et al., "Current and future approaches to lumbar disc surgery: A literature review", *Medscape Orthopedics & Sports Medicine*, 1, [www.medscape.com/Medscape/OrthoSportsMed/1997/v01.n 11/.../mos3057], (1997).

(Continued)

*Primary Examiner*—Pedro Philogene
(74) *Attorney, Agent, or Firm*—Jonathan Spangler

(57) ABSTRACT

A bone block for insertion into a patient's intervertebral space. A method for inserting a bone block into a patient's intervertebral space, comprising: supporting the bone block in an inserter; advancing the inserter into the intervertebral space; rotating the inserter, thereby separating adjacent vertebrae; separating the bone block and the inserter with a push rod; and removing the inserter from the intervertebral space.

19 Claims, 26 Drawing Sheets

U.S. PATENT DOCUMENTS

| | | |
|---|---|---|
| 4,877,020 A | 10/1989 | Vich |
| 4,878,915 A | 11/1989 | Brantigan |
| 4,932,975 A | 6/1990 | Main et al. |
| 4,961,740 A | 10/1990 | Ray et al. |
| 4,962,766 A | 10/1990 | Herzon |
| 5,026,373 A | 6/1991 | Ray et al. |
| 5,055,104 A | 10/1991 | Ray |
| 5,062,845 A | 11/1991 | Kuslich et al. |
| 5,092,572 A | 3/1992 | Litwak et al. |
| 5,133,717 A | 7/1992 | Chopin |
| 5,133,755 A | 7/1992 | Brekke |
| 5,171,278 A | 12/1992 | Pisharod |
| 5,192,327 A | 3/1993 | Brantigan |
| 5,217,497 A | 6/1993 | Mehdian |
| 5,269,785 A | 12/1993 | Bonutti |
| 5,284,153 A | 2/1994 | Raymond et al. |
| 5,290,494 A | 3/1994 | Coombes et al. |
| 5,300,076 A | 4/1994 | Leriche |
| 5,304,210 A | 4/1994 | Crook |
| 5,306,307 A | 4/1994 | Senter et al. |
| 5,306,309 A | 4/1994 | Wagner et al. |
| 5,322,505 A | 6/1994 | Krause et al. |
| 5,334,205 A | 8/1994 | Cain |
| 5,336,223 A | 8/1994 | Rogers |
| 5,364,400 A | 11/1994 | Rego, Jr. et al. |
| 5,395,372 A | 3/1995 | Holt et al. |
| 5,397,363 A | 3/1995 | Gelbard |
| 5,405,391 A | 4/1995 | Henderson et al. |
| 5,413,602 A | 5/1995 | Metz-Stavenhagen |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,445,639 A | 8/1995 | Kuslich et al. |
| 5,454,811 A | 10/1995 | Huebner |
| 5,458,638 A | 10/1995 | Kuslich et al. |
| 5,484,403 A | 1/1996 | Yoakum et al. |
| 5,489,308 A | 2/1996 | Kuslich et al. |
| 5,505,732 A * | 4/1996 | Michelson .................. 606/61 |
| 5,522,879 A | 6/1996 | Scopelianos |
| 5,522,899 A | 6/1996 | Michelson |
| 5,524,624 A | 6/1996 | Tepper et al. |
| 5,527,312 A | 6/1996 | Ray |
| 5,534,029 A * | 7/1996 | Shima .................. 623/17.15 |
| 5,534,030 A | 7/1996 | Navarro et al. |
| 5,540,688 A | 7/1996 | Navas |
| 5,545,222 A | 8/1996 | Bonutti |
| 5,562,736 A | 10/1996 | Ray et al. |
| 5,565,005 A | 10/1996 | Erickson et al. |
| 5,571,190 A | 11/1996 | Ulrich |
| 5,571,192 A | 11/1996 | Schonhoffer |
| 5,593,409 A | 1/1997 | Michelson |
| 5,609,636 A | 3/1997 | Kohrs et al. |
| 5,611,800 A | 3/1997 | Davis et al. |
| 5,611,810 A | 3/1997 | Arnold et al. |
| 5,632,747 A | 5/1997 | Scarborough et al. |
| 5,645,598 A | 7/1997 | Brosnahan et al. |
| 5,653,761 A | 8/1997 | Pisharodi |
| 5,653,762 A | 8/1997 | Pisharodi |
| 5,658,336 A | 8/1997 | Pisharodi |
| 5,658,337 A | 8/1997 | Kohrs et al. |
| 5,662,710 A | 9/1997 | Bonutti |
| 5,665,122 A | 9/1997 | Kambin |
| 5,669,909 A | 9/1997 | Zdeblick et al. |
| 5,676,703 A | 10/1997 | Gelbard |
| 5,683,394 A * | 11/1997 | Rinner .................. 606/86 |
| 5,683,400 A | 11/1997 | McGuire |
| 5,683,464 A | 11/1997 | Wagner et al. |
| 5,690,629 A | 11/1997 | Asher et al. |
| 5,700,264 A | 12/1997 | Zucherman et al. |
| 5,700,291 A | 12/1997 | Kuslich et al. |
| 5,700,292 A | 12/1997 | Margulies |
| 5,702,449 A | 12/1997 | McKay |
| 5,702,451 A | 12/1997 | Biedermann et al. |
| 5,702,453 A | 12/1997 | Rabbe et al. |
| 5,702,454 A | 12/1997 | Baumgartner |
| 5,702,455 A | 12/1997 | Saggar |
| 5,703,451 A | 12/1997 | Yamamichi et al. |
| 5,707,373 A | 1/1998 | Sevrain et al. |
| 5,711,957 A | 1/1998 | Patat et al. |
| 5,716,415 A | 2/1998 | Steffee |
| 5,720,748 A | 2/1998 | Kuslich et al. |
| 5,720,751 A | 2/1998 | Jackson |
| 5,723,013 A * | 3/1998 | Jeanson et al. .......... 623/17.16 |
| 5,741,261 A | 4/1998 | Moskovitz et al. |
| 5,755,797 A | 5/1998 | Baumgartner |
| 5,766,252 A | 6/1998 | Henry et al. |
| 5,772,661 A | 6/1998 | Michelson |
| 5,775,331 A | 7/1998 | Raymond et al. |
| 5,779,642 A | 7/1998 | Nightengale |
| 5,782,830 A | 7/1998 | Farris |
| 5,782,919 A | 7/1998 | Zdeblick et al. |
| 5,785,710 A | 7/1998 | Michelson |
| 5,797,909 A | 8/1998 | Michelson |
| 5,800,549 A | 9/1998 | Bao et al. |
| 5,800,550 A * | 9/1998 | Sertich .................. 623/17.16 |
| 5,814,084 A | 9/1998 | Grivas et al. |
| 5,851,208 A | 12/1998 | Trott |
| 5,865,845 A | 2/1999 | Thalgott |
| 5,865,847 A * | 2/1999 | Kohrs et al. .................. 128/898 |
| 5,865,848 A | 2/1999 | Baker |
| 5,885,299 A | 3/1999 | Winslow et al. |
| 5,888,219 A | 3/1999 | Bonutti |
| 5,888,224 A | 3/1999 | Beckers et al. |
| 5,893,890 A | 4/1999 | Pisharodi |
| 5,904,719 A | 5/1999 | Errico et al. |
| 5,910,315 A | 6/1999 | Stevenson et al. |
| 5,954,769 A | 9/1999 | Rosenlicht |
| 5,961,554 A * | 10/1999 | Janson et al. ............ 623/17.16 |
| 5,968,098 A | 10/1999 | Winslow |
| 5,993,474 A | 11/1999 | Ouchi |
| 6,004,326 A | 12/1999 | Castro et al. |
| 6,015,436 A | 1/2000 | Schunhuffer |
| 6,033,405 A | 3/2000 | Winslow et al. |
| 6,039,761 A | 3/2000 | Li et al. |
| 6,042,582 A | 3/2000 | Ray |
| 6,045,580 A | 4/2000 | Scarborough et al. |
| 6,048,342 A | 4/2000 | Zucherman et al. |
| 6,059,790 A * | 5/2000 | Sand et al. .................. 606/99 |
| 6,063,088 A | 5/2000 | Winslow |
| 6,083,225 A | 7/2000 | Winslow et al. |
| 6,096,080 A | 8/2000 | Nicholson et al. |
| 6,102,948 A | 8/2000 | Brosnahan, III |
| 6,120,506 A | 9/2000 | Kohrs et al. |
| 6,132,472 A | 10/2000 | Bonutti |
| 6,159,211 A | 12/2000 | Boriani et al. |
| 6,159,215 A | 12/2000 | Urbahns et al. |
| 6,193,756 B1 | 2/2001 | Studer et al. |
| 6,200,347 B1 | 3/2001 | Anderson et al. |
| 6,224,607 B1 | 5/2001 | Michelson |
| 6,224,631 B1 | 5/2001 | Kohrs |
| 6,241,769 B1 | 6/2001 | Nicholson et al. |
| 6,241,771 B1 | 6/2001 | Gresser et al. |
| 6,251,140 B1 | 6/2001 | Marino et al. |
| 6,258,125 B1 | 7/2001 | Paul et al. |
| 6,277,149 B1 | 8/2001 | Boyle et al. |
| 6,319,257 B1 | 11/2001 | Carignan et al. |
| 6,371,989 B1 | 4/2002 | Chauvin et al. |
| 6,440,142 B1 | 8/2002 | Ralph et al. |
| 6,442,814 B1 | 9/2002 | Landry et al. |
| 6,454,806 B1 | 9/2002 | Cohen et al. |
| 6,527,773 B1 | 3/2003 | Lin et al. |
| 6,595,998 B2 | 7/2003 | Johnson et al. |
| 6,635,086 B2 | 10/2003 | Lin |

| | | | |
|---|---|---|---|
| 6,648,895 B2 | 11/2003 | Burkus et al. | |
| 6,887,248 B2 | 5/2005 | McKinley et al. | |
| 2002/0058950 A1 | 5/2002 | Winterbottom et al. | |
| 2003/0105528 A1 | 6/2003 | Shimp et al. | |

FOREIGN PATENT DOCUMENTS

| | | |
|---|---|---|
| EP | 369603 | 5/1990 |
| EP | 517030 | 5/1992 |
| EP | 667127 | 8/1995 |
| EP | 706876 | 4/1996 |
| EP | 716840 | 6/1996 |
| EP | 737448 | 10/1996 |
| EP | 796593 | 9/1997 |
| EP | 880938 | 2/1998 |
| EP | 809974 | 4/1998 |
| EP | 809975 | 4/1998 |
| EP | 811356 | 4/1998 |
| WO | WO-91/06261 | 5/1991 |
| WO | WO-94/04100 | 3/1994 |
| WO | WO-94/10928 | 5/1994 |
| WO | WO-95/01810 | 1/1995 |
| WO | WO-96/08205 | 3/1996 |
| WO | WO-96/17564 | 3/1996 |
| WO | WO-96/41582 | 12/1996 |
| WO | WO-97/20513 | 6/1997 |
| WO | WO-97/33525 | 9/1997 |
| WO | WO-97/37620 | 10/1997 |
| WO | WO-98/09586 | 3/1998 |
| WO | WO-98/14142 | 4/1998 |
| WO | WO-98/17208 | 4/1998 |
| WO | WO-98/25539 | 6/1998 |
| WO | WO-99/08627 | 2/1999 |
| WO | WO-99/38461 | 8/1999 |
| WO | WO-00/45712 | 8/2000 |
| WO | WO-00/45713 | 8/2000 |
| WO | WO-01/41681 | 6/2001 |
| WO | WO-01/49333 | 7/2001 |

OTHER PUBLICATIONS

Benini, et al., "Undercutting decompression and posterior fusion with translaminar facet screw fixation in degenerative lumbar spinal stenosis: Technique and results", *Neuro-Orthopedics*, (1995), 159-172.

Kambin, et al., "History and current status of percutaneous arthroscopic disc surgery", *Spine*, 21, (1996), 57S-61S.

Stein, et al. "Percutaneous facet joint fusion: Preliminary experience", *Journal of Vascular and Interventional Radiology*, 4, (1993), 69-74.

Vamvanij, et al., "Surgical treatment of internal disc disruption: An outcome study of four fusion techniques", *Journal of Spinal Disorders*, 4, (1998), 375-382.

* cited by examiner

SPINAL IMPLANTS AND METHODS FOR INSERTING SPINAL IMPLANTS INTO INTERVERTEBRAL SPACES

CROSS-REFERENCES TO RELATED APPLICATIONS

The present application is a division of commonly owned and U.S. patent application Ser. No. 10/032,121, filed on Dec. 21, 2001, and issued as U.S. Pat. No. 6,887,248, which is a divisional application of commonly owned and U.S. patent application Ser. No. 09/320,081, filed on May 26, 1999 and issued as U.S. Pat. No. 6,368,325, which claims benefit under 35 U.S.C. §119(e) from U.S. Provisional Patent Application Ser. No. 60/086,945, filed on May 27, 1998, U.S. Provisional Patent Application Ser. No. 60/113,651, filed on Dec. 23, 1998, and U.S. Provisional Patent Application Ser. No. 60/120,663, filed on Feb. 19, 1999, the complete disclosures of which are hereby incorporated herein by reference in their entirety for all purposes.

TECHNICAL FIELD

The present invention relates to bone block implants which promote bone fusion between adjacent vertebrae.

BACKGROUND OF THE INVENTION

Intervertebral spinal inserts are used to provide support and maintain normal distance between adjacent vertebrae in cases where a patient's vertebral discs have degenerated. Such degeneration can occur as a result of aging or trauma and typically results in pinched or damaged nerves between or proximal to the adjacent vertebrae. Moreover, such discal degeneration causes shifting of the loading along the patient's spinal column, which in turn further accelerates the vertebral degeneration.

Intervertebral inserts are typically used to reestablish normal intervertebral spacing and to cause fusion between adjacent vertebral bodies.

A common problem with the existing intervertebral spinal inserts is that they do not provide stabilization in two perpendicular directions in the plane of the patient's intervertebral space.

Another disadvantage is that, during such major surgery, the actual insertion of the intervertebral insert requires distraction of the adjacent vertebrae to first open a sufficiently large passage for the insertion of the insert therebetween. Such distraction is typically performed by dedicated instrumentation and invasive tools which must first enter the intervertebral space and then grip and hold apart the adjacent vertebrae.

SUMMARY OF THE INVENTION

The present invention provides methods and devices for inserting a bone block into a patient's intervertebral space wherein the bone block is supported in an inserter which is first advanced into the intervertebral space. After the inserter is received into the patient's intervertebral space, the inserter is then rotated by approximately 90°. Convexly curved outer camming surfaces on the inserter operate to separate the adjacent vertebrae as the inserter is rotated by 90°. Rotation of the inserter by 90° also operates to orient the bone block in a preferred orientation relative to the opposite vertebral surfaces. An illustration of camming apart adjacent vertebrae using an outwardly facing convexly curved camming surfaces is set forth in provisional patent application Ser. Nos. 60/086,945 filed May 27, 1998; 60/113,651 filed Dec. 23, 1998; and 60/120,663 filed Feb. 19, 1999; incorporated herein by reference in their entirety.

Specifically, the outwardly facing convexly curved camming surfaces are adapted to engage, and to separate by camming action, the opposed adjacent vertebrae when the bone block is initially placed between the vertebrae and then subsequently rotated by 90°. After the bone block is rotated into position, it supports the spinal load, thereby easing pressure on the vertebral disc and surrounding tissue. As such, prior distraction of the adjacent vertebrae with dedicated instrumentation is either not required, or is substantially minimized.

After the bone block is rotated into an anchored position between the adjacent vertebrae, the inserter is withdrawn from the intervertebral space leaving the bone block in a preferred position to promote bone fusion between the adjacent vertebrae. In a preferred aspect, the bone block is held stationery by a push rod, (which is preferably received in an inner cannulated passageway in the inserter), and the inserter, (preferably positioned thereover), is withdrawn such that the bone block is pushed out of the distal end of the inserter.

In preferred aspects, the bone block is dimensioned to extend to a height greater than that of the inserter such that vertebral supporting surfaces of the bone block anchor against the adjacent vertebrae to facilitate removal of the bone block from the inserter, reducing or eliminating the requirement of a push rod separating the bone block from the inserter.

The present bone blocks can be used singly, in pairs, or in quartets. When used in pairs or quartets, the bone blocks can be angled with respect to one another such that increased vertebral stability is achieved. Similarly, more than four bone blocks can be uses, and the present invention therefore also encompasses using 6, 8, 10 or more bone blocks to provide intervertebral stability.

In a first preferred aspect of the invention, the inserter is received through a cannula which is percutaneously introduced into the patient in a posterolateral approach. Also in preferred aspects of the invention, the cannula has an oval or racetrack shaped cross-section and the inserter received therein has a truncated oval shaped cross-section.

In an alternate aspect of the invention, a separate cannula with an inserter received therethrough is instead replaced by a single unit, being an oval shaped cannula which is dimensioned to support a bone block at its distal end. In this aspect of the present invention, the outwardly facing camming surfaces which operate to cam apart the adjacent vertebrae are disposed on the distal end of the cannula itself and the vertebrae are cammed apart as the cannula is rotated by 90°.

An important advantage of the present invention is that it provides a system for implanting bone blocks in a patient's intervertebral space in a minimally invasive surgical procedure. In contrast, current interbody fusion devices are typically implanted during open surgery.

An advantage of approaching posteriolaterally in a minimally invasive procedure is that the passive elements of spinal stability (anterior and posterior longitudinal ligaments, interspinous ligaments, and facet capsule) are not disturbed and provide stability when stretched by the insertion of the bone block.

The present invention also provides methods for positioning first and second bone blocks in the patients intervertebral space. Preferably, the first and second bone blocks are disposed with their central longitudinally extending axes at an angle to one another so as to give increased vertebral stability. In this aspect of the invention, each of the bone blocks are preferably introduced through percutaneous cannula which are oriented in opposite posterolateral approaches, being disposed at about 70° to 135°, and most preferably 90°, to one another.

In various aspects of the invention, the first and second bone blocks may optionally be interlocked together in the patient's intervertebral space. In such aspects of the invention, the first and second bone blocks may be interlocked by a variety of techniques including suturing the blocks together, interlocking a protrusion on the first bone block with an aperture on the second bone block or by interlocking a notch on the first bone block with a groove on the second bone block. In addition, the first and second bone blocks may be fastened together by a fastening pin.

The present invention also provides a system for introducing a bone block into an intervertebral space comprising a two pronged inserter wherein each prong has an outwardly facing convexly curved camming surface for separating adjacent vertebrae and wherein each prong is disposed on opposite sides of the bone block positioned therebetween. The bone block may preferably have lateral protrusions which extend in a longitudinal direction along the length of the bone block. In this aspect, the lateral protrusions on the bone block preferably mate with longitudinally extending grooves on the inner surfaces of the prongs, thereby preventing unwanted motion of the bone block, but permitting the bone block to be slid axially out of the distal end of the inserter.

An advantage of the present system is that the bone block inserter protects the bone block during insertion, and distracts the adjacent vertebrae by camming action to gain the needed space for placement of the bone block. By distracting the adjacent vertebral bodies, the present invention also decompresses the nerves that may be causing pain.

In another aspect of the present invention, a bone block is provided having opposite vertebral contact surfaces with opposite sides spanning between the vertebral contact surfaces, wherein the opposite vertebral contact surfaces each have a width which is about 20% to 60%, and most preferably 30% of the height of the opposite sides spanning between the opposite vertebral contact surfaces. In this aspect of the invention, a tall, narrow bone block is provided for positioning between adjacent vertebrae.

In preferred aspects, the opposite vertebral support surfaces of the bone block can be angled with respect to one another to restore a patient's lordotic angle.

An advantage of the present bone block relative to existing cortical bone blocks is its novel shape which uses substantially less human tissue. Specifically, the present bone block uses ⅓ to ⅕ the amount of human tissue currently used in existing bone block implants. The advantage of using less human tissue is important in the business of bone banks as the supply of donor tissue is quite limited. The present bone block may preferably comprise any suitable bone material including autologous, allographic, xenographic, or other osteoinductive and osteoproliferative elements.

Another advantage of the present system is that the bone block is placed between the vertebral endplates to rest upon cortical bone. In contrast, current fusion cages and cortical bone blocks require predrilling and partial destruction of the vertebral endplates. This predrilling removes cortical bone from the endplate thereby increasing the likelihood of subsidence or the sinking of the bone block into the vertebral body.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DEFINITIONS

As used herein, the following terms are understood to have the following meanings:

"camming"—increasing intervertebral separation by rotating opposite convexly curved sides of an intervertebral insert against adjacent vertebrae.

"distraction"—pulling apart, separating, or increasing the distance between adjacent opposite vertebrae by physical or mechanical means.

"fusion"—complete ingrowth of bone tissue between adjacent vertebrae.

"outwardly facing convexly curved camming surface"—a surface having a degree of curvature corresponding to an arc section defined by an angle in the range of 15 to 40 degrees, and most preferably about 20 degrees.

"posterolateral"—behind and to one side.

"racetrack-shaped"—a shape having two elongated parallel sides and two curved ends.

DESCRIPTION OF THE SPECIFIC EMBODIMENTS

The present invention provides a novel system for inserting and positioning one or two bone blocks between adjacent vertebrae.

Figure 1:
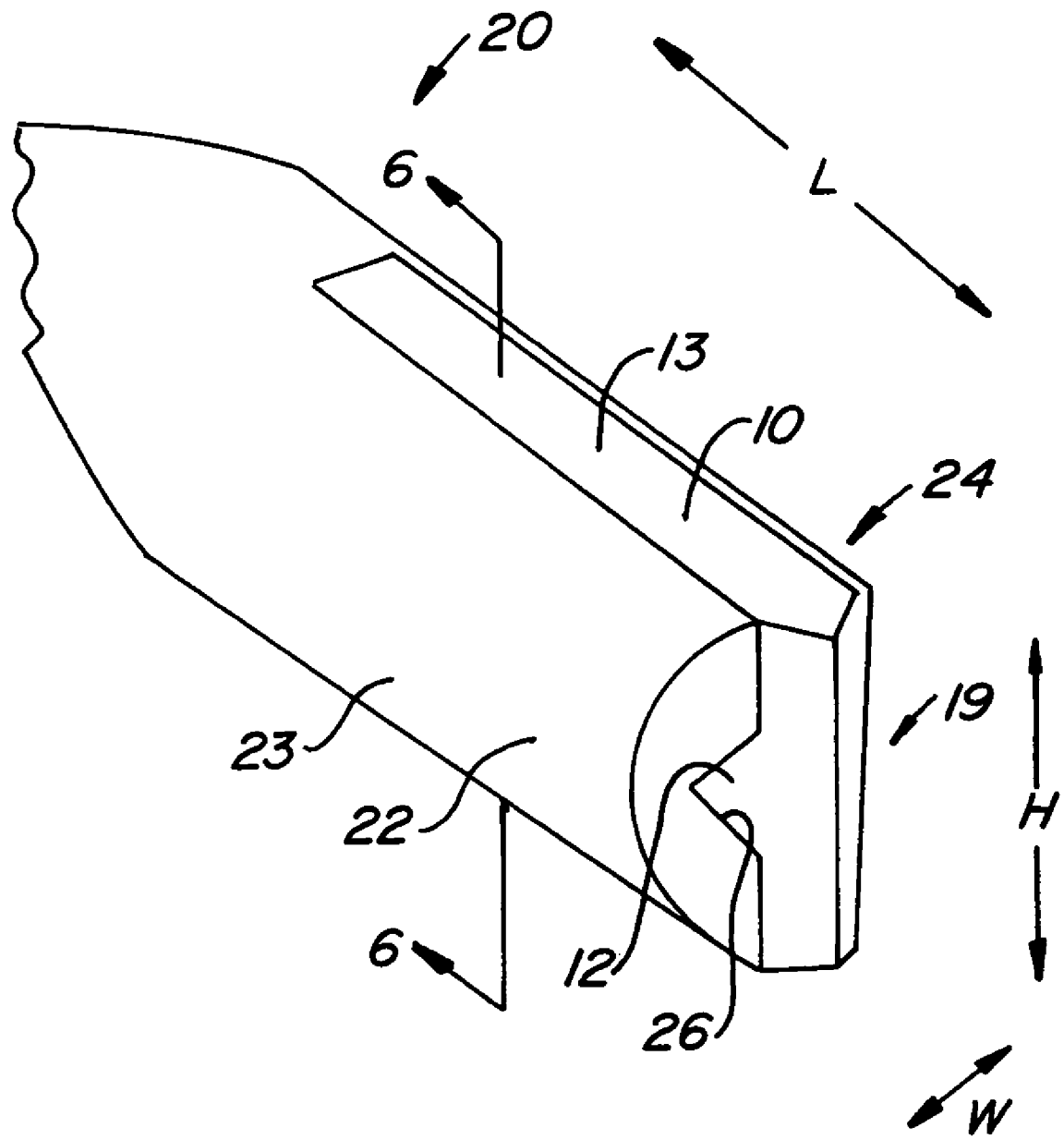
FIG. 1 is a perspective view of a bone block inserter holding a bone block therein.

Referring to FIG. 1, a novel shaped bone block 10 is held between opposite prongs 22 and 24 of bone block inserter 20. Bone block 10 is formed from donor bone tissue, and operates to conduct bone fusion between adjacent vertebrae after it has been implanted between the vertebrae by inserter 20, as will be explained. Prongs 22 and 24 each have curved outer surfaces 23 and 25, respectively, and inner longitudinally extending grooves 26 and 28, (seen more clearly in FIG. 3), respectively.

Figure 3:
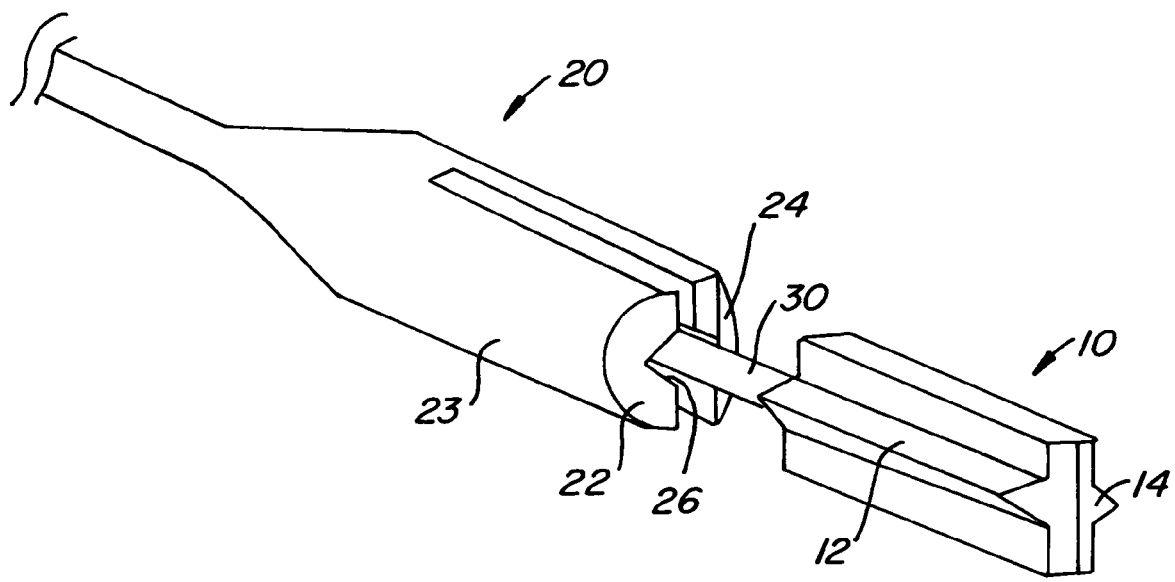
FIG. 3 is a perspective view of the system of FIG. 1, showing removal of the bone block from the inserter by a push rod.

Subsequent to placement between adjacent vertebrae, (as will be explained more fully herein), bone block 10 is removed from inserter 20. In a preferred aspect, as shown in FIG. 3, a push rod 30 is preferably received within a longitudinally extending central bore (not shown) in inserter 20. As such, bone block 10 can be held at a fixed position between the adjacent vertebrae by holding push rod 30 at a fixed location while inserter 20 is slipped back over push rod 30 and thereby withdrawn from the intervertebral space.

Figure 6:
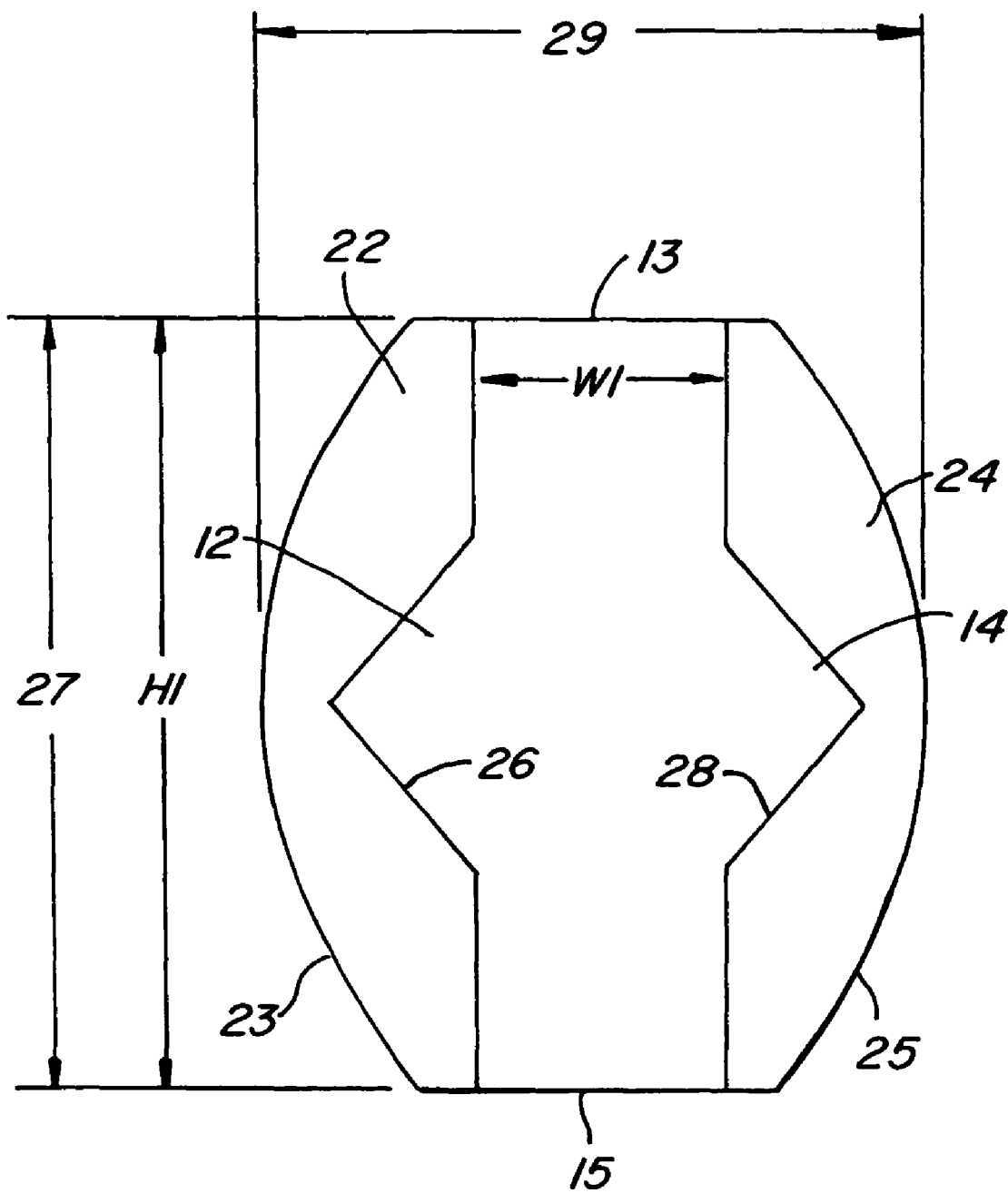
FIG. 6 is a cross-sectional view of the bone block and inserter taken along line 6-6 in FIG. 1.

As can be seen in FIGS. 3 and 6, bone block 10 preferably has laterally extending protrusions 12 and 14 which slidably mate with inner grooves 26 and 28 which extend longitudinally along the inner surfaces of prongs 22 and 24 as shown.

Protrusions 12 and 14 serve several functions. First, they anchor bone block 10 within inserter 20 such that bone block 10 does not slide laterally out of inserter 20. Secondly, protrusions 12 and 14 are designed to absorb or withstand forces generated by rotation of inserter 20. Such rotational forces will tend to twist the distal end of inserter prongs 22 and 24 (relative to the proximal end of inserter 20). This twisting is significantly reduced or eliminated by mating of the implant and inserter as described.

Preferably, bone block 10 and inserter 20 may be designed to display an angled front end 19 when assembled together (FIGS. 1 and 2) which assists during insertion of the inserter and bone block into the patient's intervertebral space.

Figure 4:
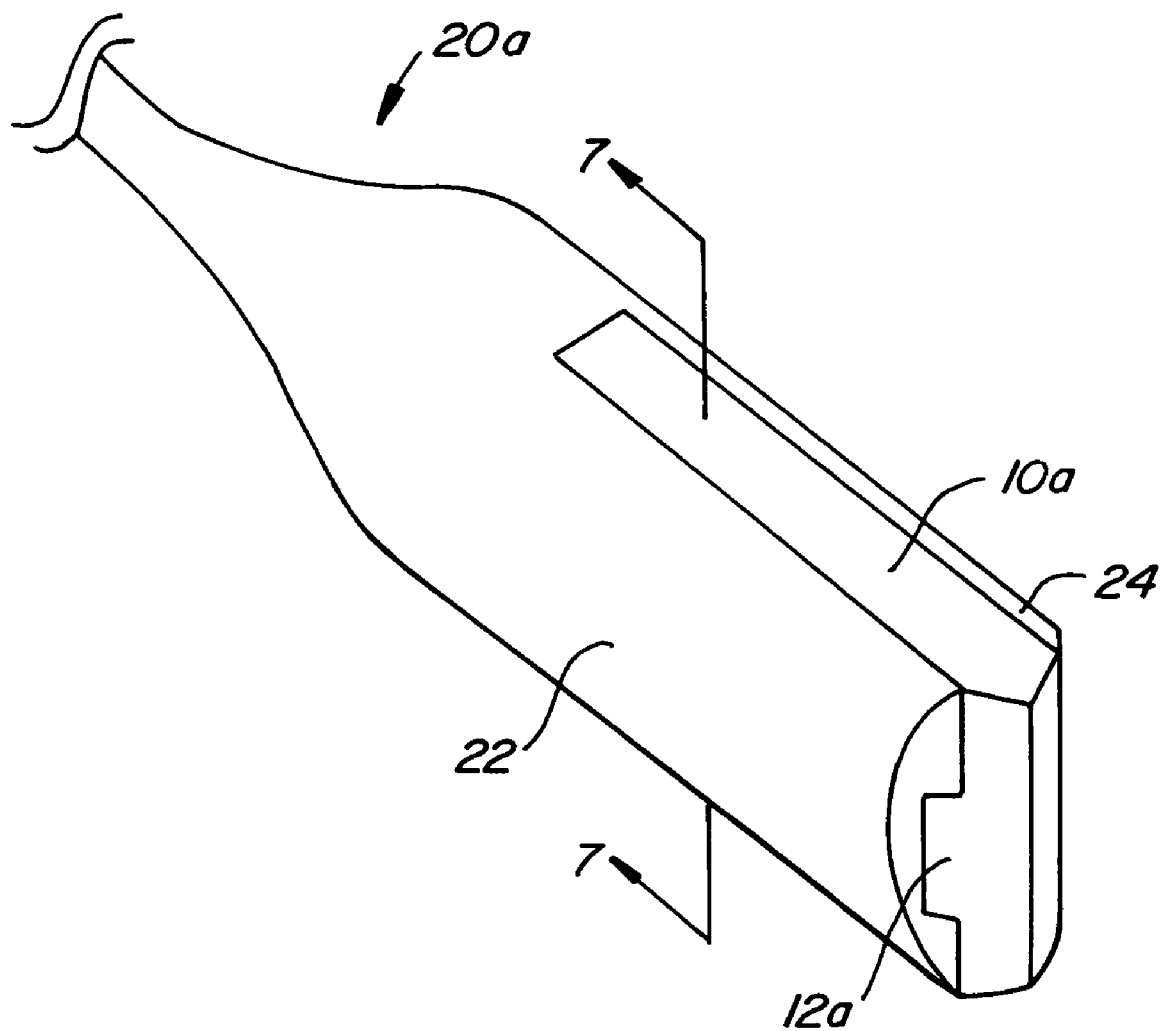
FIG. 4 is a perspective view of an alternately shaped inserter and bone block.
Figure 5:
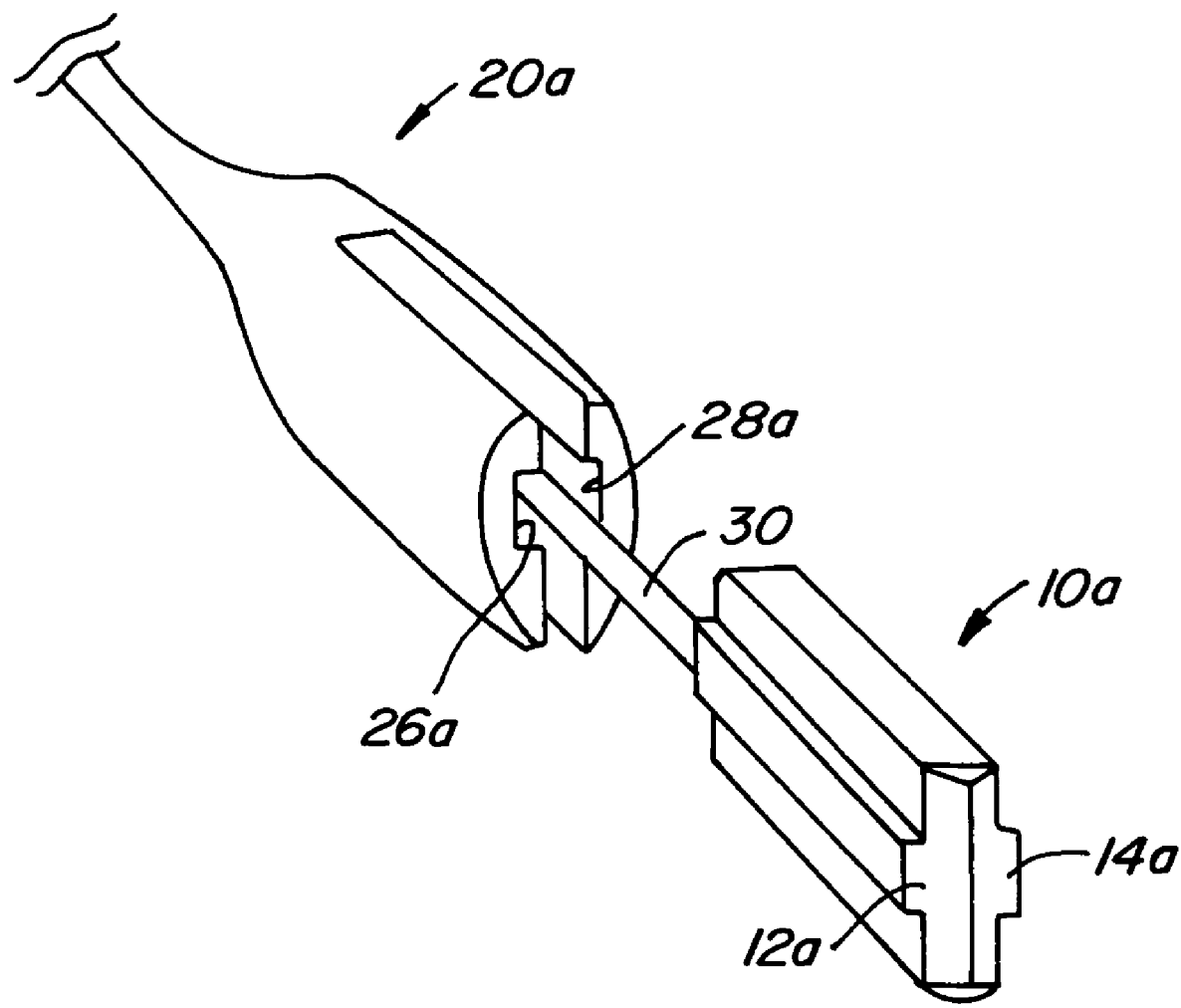
FIG. 5 is a view corresponding to FIG. 4, showing removal of the bone block from the inserter.
Figure 7:
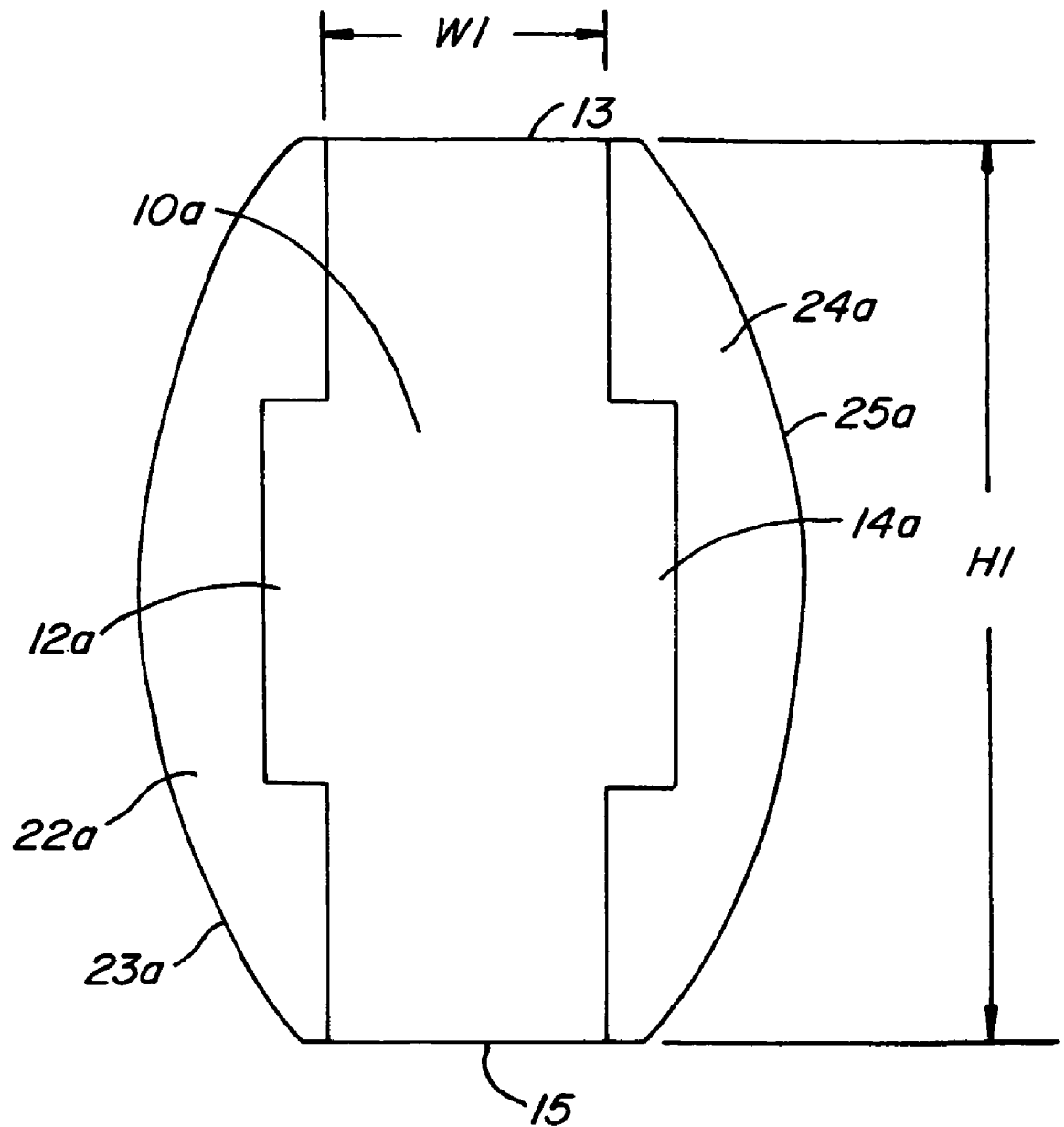
FIG. 7 is a cross-sectional view of a bone block and inserter taken along line 7-7 in FIG. 4.

FIGS. 4, 5, and 7 show an alternate shape of bone block with bone block 10a having rectangular shaped lateral protrusions 12a and 14a which are slidably received in grooves 26a and 28a of inserter 20a. The fabrication of rectangular shaped lateral protrusions 12a and 14a offer the advantages of ease of manufacture and absorption of shear stresses from rotation of inserter 20a.

The present invention also provides a novel method for inserting a bone block between a patient's intervertebral space, as follows.

Figure 8:
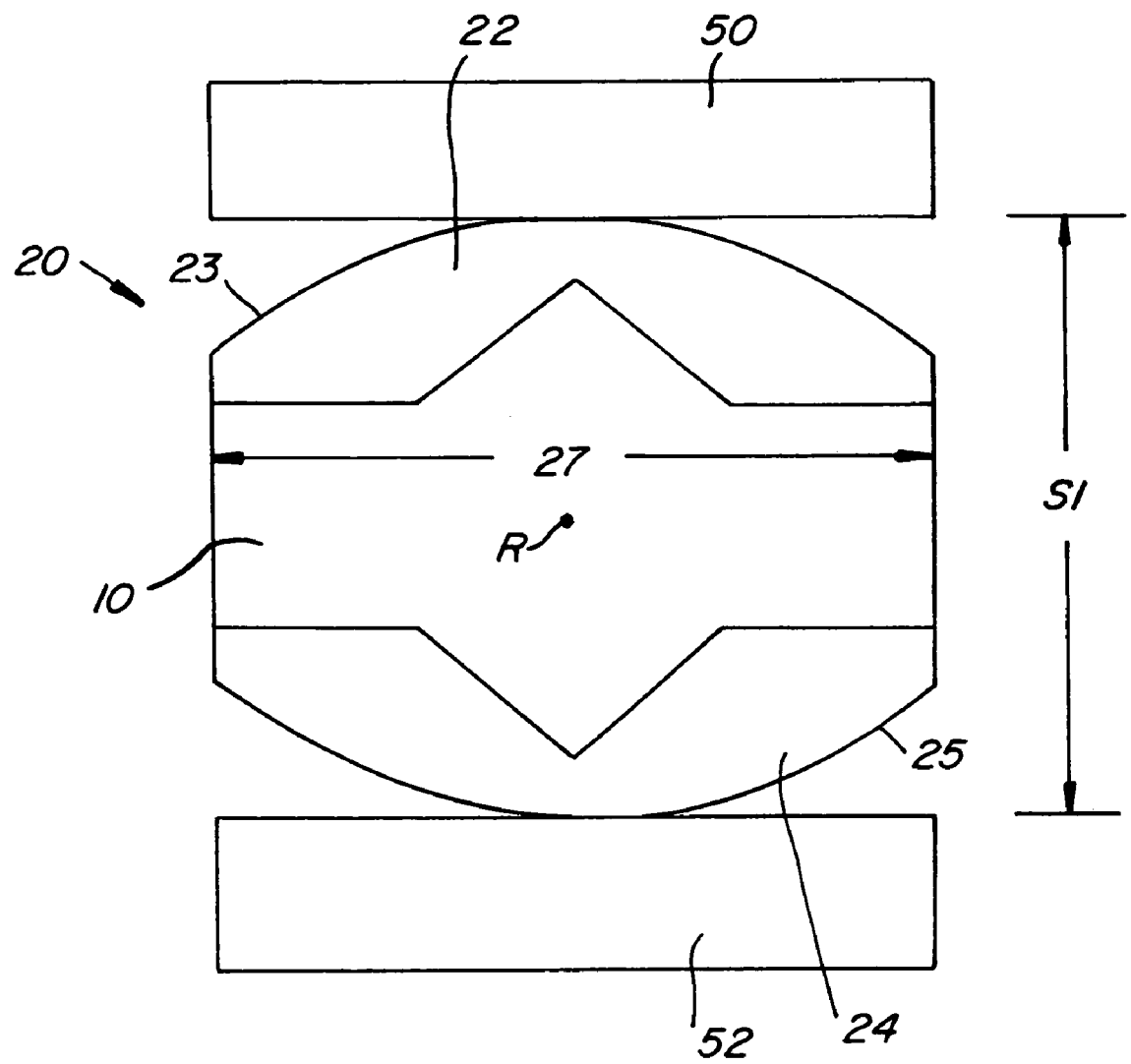
FIG. 8 shows the inserter and bone block as initially received between adjacent vertebrae.

Referring to FIG. 8, inserter 20, (which holds bone block 10 therein as shown), is received between adjacent vertebrae 50 and 52 in the orientation shown. Specifically, inserter 20 is preferably disposed with its major dimension 27 parallel to the adjacent vertebrae 50 and 52. In this orientation, inserter 20 can more easily be received into the patient's intervertebral space.

Figure 9:
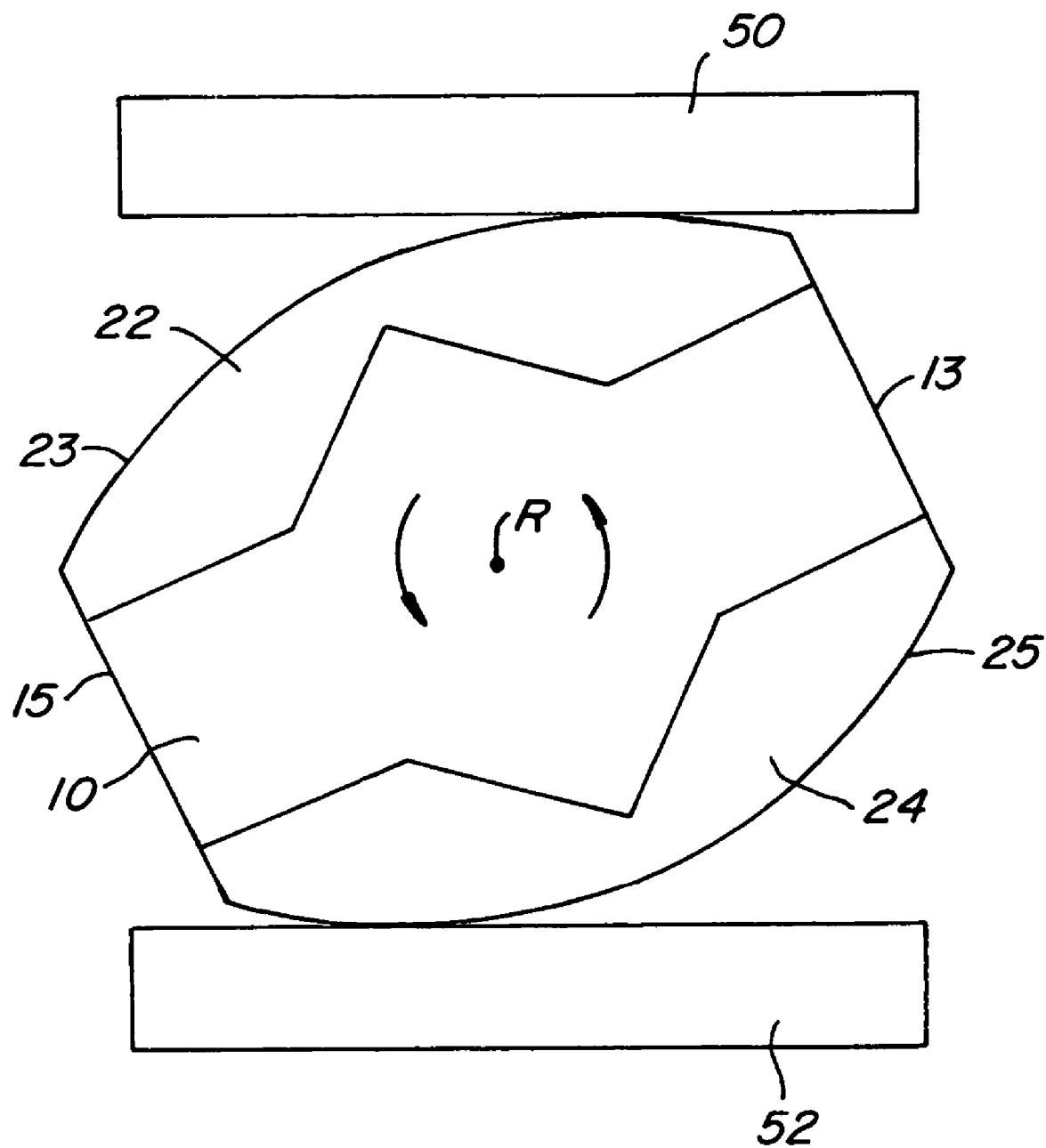
FIG. 9 shows partial rotation of the inserter of FIG. 8, with the inserter camming apart the adjacent vertebrae.
Figure 10:
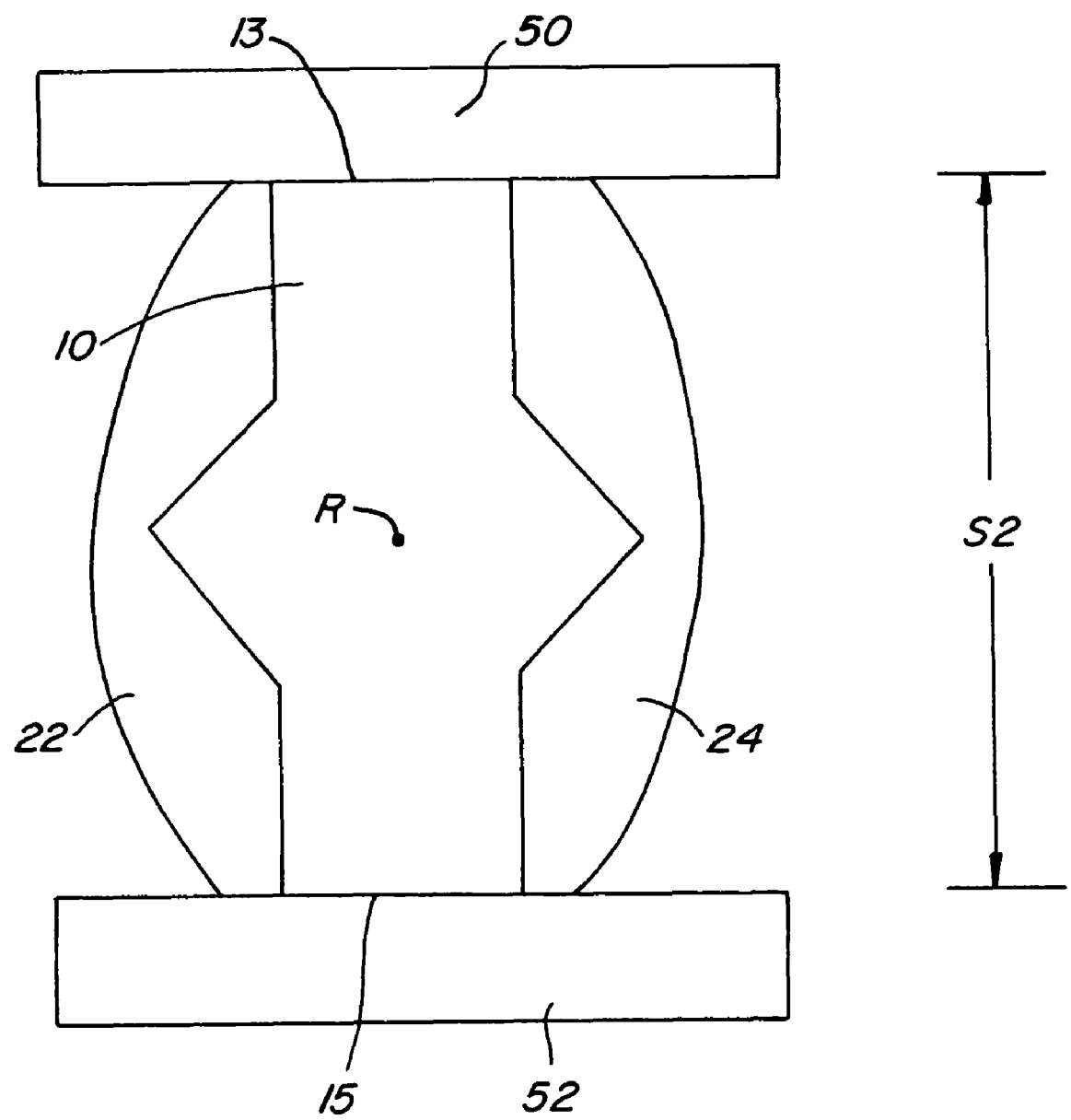
FIG. 10 shows 90° rotation of the inserter from the position of FIG. 8, showing the preferred orientation of the bone block between the fully cammed apart adjacent vertebrae.

Inserter 20 is then rotated about its central, longitudinally extending axis R from the orientation shown in FIG. 8 through to the orientations shown successively in FIGS. 9 and 10. As can be seen, the rotation of inserter 20 about axis R by 90° will cause curved outer camming surfaces 23 and 25 to cam apart adjacent vertebrae 50 and 52, thereby increasing the vertebral spacing between vertebrae 50 and 52 from smaller spacing S1 (FIG. 9) to larger spacing S2 (FIG. 10).

Surfaces 23 and 25 may preferably comprise outwardly facing convexly curved camming surfaces such as the outwardly facing convexly curved camming surfaces as fully described in provisional patent application Ser. Nos. 60/086,945 filed May 27, 1998; 60/113,651 filed Dec. 23, 1998; and 60/120,663 filed Feb. 19, 1999; incorporated herein by reference in their entirety. Surfaces 23 and 25 are disposed on opposite sides of prongs 22 and 24 of inserter 20 as shown and are adapted to engage, and to separate by camming action, the opposed vertebral surfaces when inserter 20 (with bone block 10 received therein), is placed between adjacent vertebrae and rotated. The degree of curvature of outwardly facing convex surfaces 23 and 25 is dimensioned to represent an arc segment in the range of 15 to 40 degrees, and is most preferably about 20 degrees. Although surfaces 23 and 25 may preferably be convexly curved as described, the present invention is not so limited and may also encompass camming designs having a more rounded or more flattened camming surfaces, including planar camming surfaces.

Figure 11A:
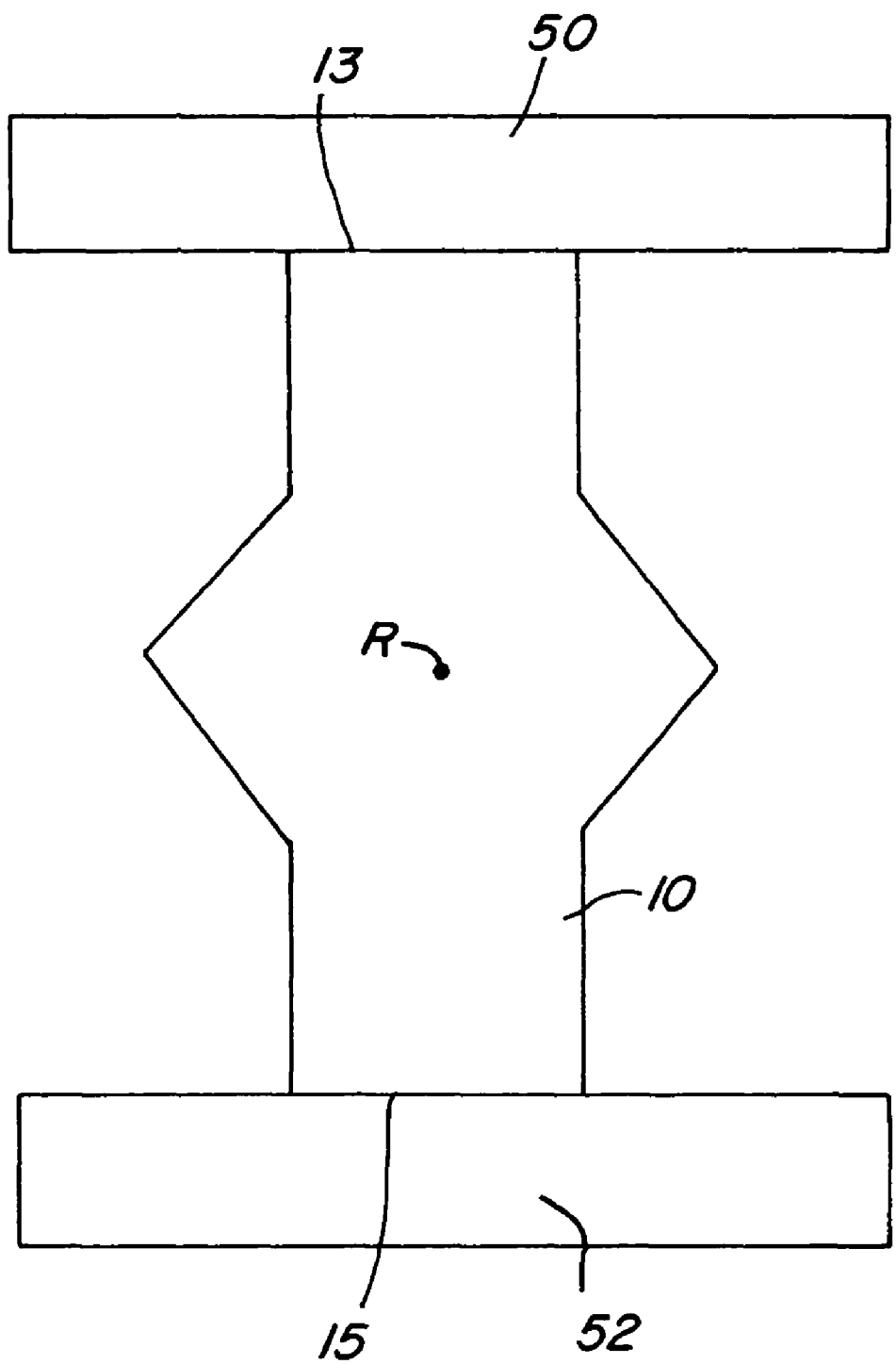
FIG. 11A corresponds to FIG. 10, but with the inserter removed, leaving the bone block in its preferred orientation between the adjacent vertebrae.

Subsequent to inserter 20 being oriented as shown in FIG. 10, bone block 10 is then removed from inserter 20 as shown in FIGS. 3 and 11A. In one aspect of the invention, push rod 30, (which is preferably received within a longitudinally extending central bore (not shown) in inserter 20), is held stationery thereby holding bone block 10 at a fixed location between vertebrae 50 and 52 which inserter 20 is withdrawn from the intervertebral space, leaving bone block 10 in position between adjacent vertebrae 50 and 52 as shown in FIG. 11A.

As can be seen in FIG. 6, opposite flattened vertebral contact surfaces 13 and 15 are disposed between outwardly facing convex surfaces 23 and 25. As will be explained in conjunction with a preferred method described herein, opposite flattened surfaces 13 and 15 are adapted to provide a flush contact against and thereby buttress adjacent separated vertebrae 50 and 52 after bone block 20 has been rotated into position.

Figure 11B:
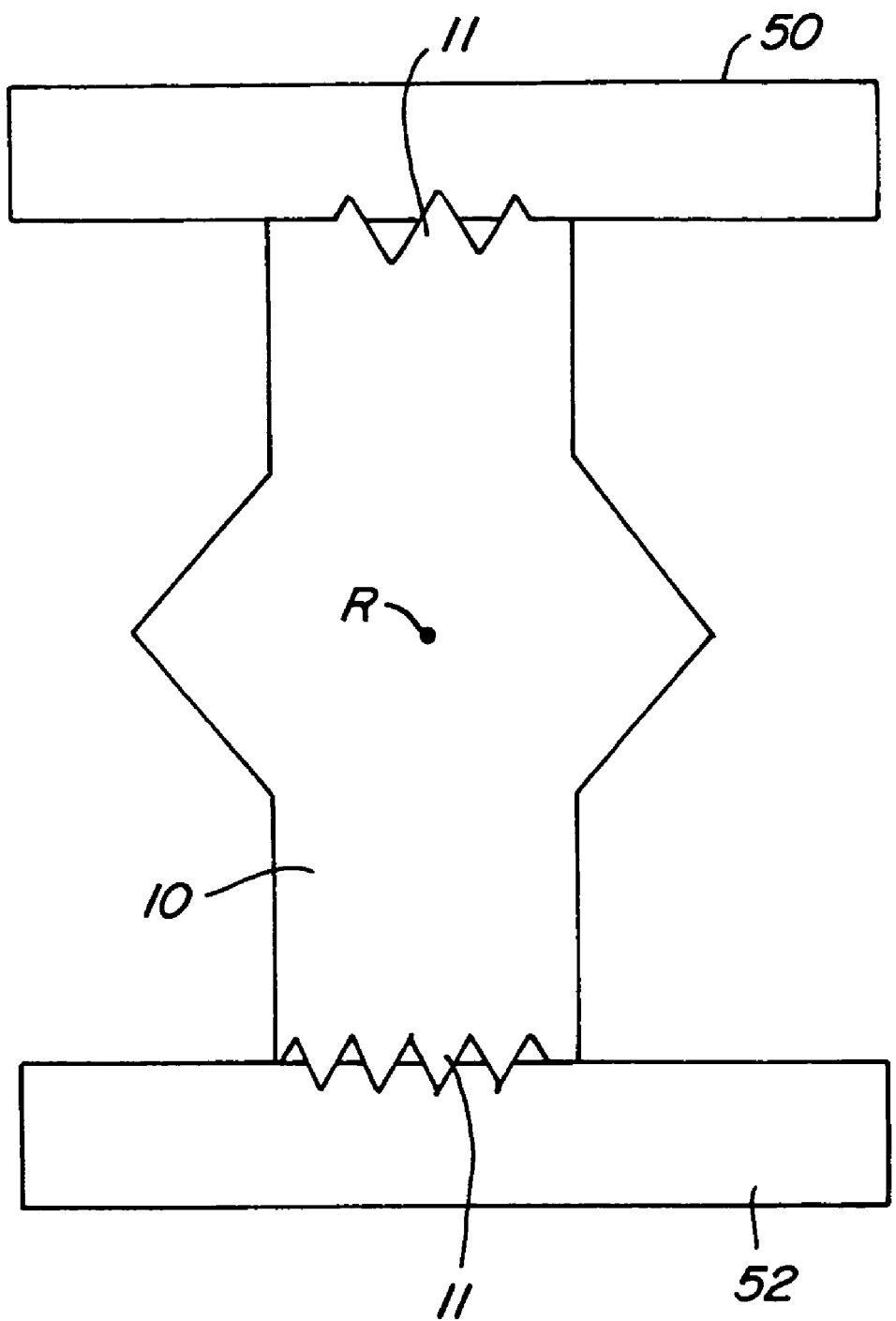
FIG. 11B shows a bone block having anchoring fins projecting into the surfaces of adjacent vertebrae.

FIG. 11B shows bone block 10 with optional anchoring fins 11 projecting into the surface of vertebrae 50 and 52, thereby holding bone block 10 in a firmly anchored position.

Push rod 30 may be threadably received into a bore (not shown) extending partially into bone block 10, such that rotation of push rod 30 will cause it to become unscrewed from bone block 10. Accordingly, push rod 30 can be controllably detached from bone block 10 and removed from the patient's intervertebral space leaving bone block 10 in position.

Figure 24:
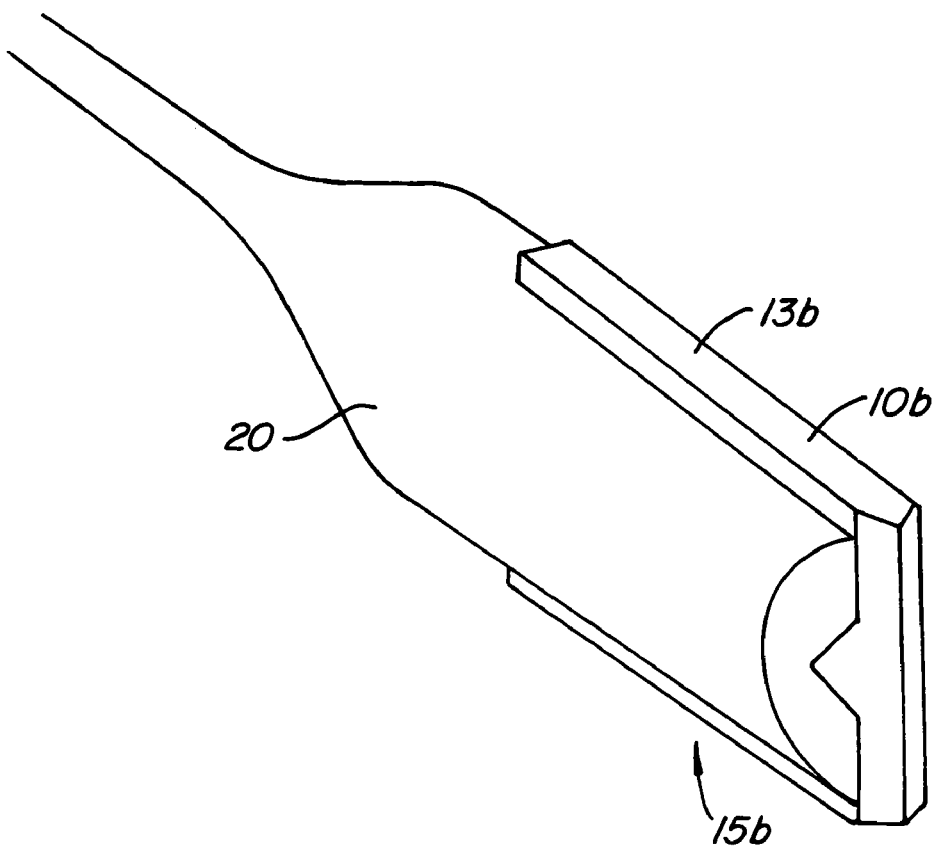
FIG. 24 is a view similar to FIG. 1, but with the vertebral contact surfaces of the bone block dimensioned to extend slightly beyond the major dimension of the inserter.
Figure 25:
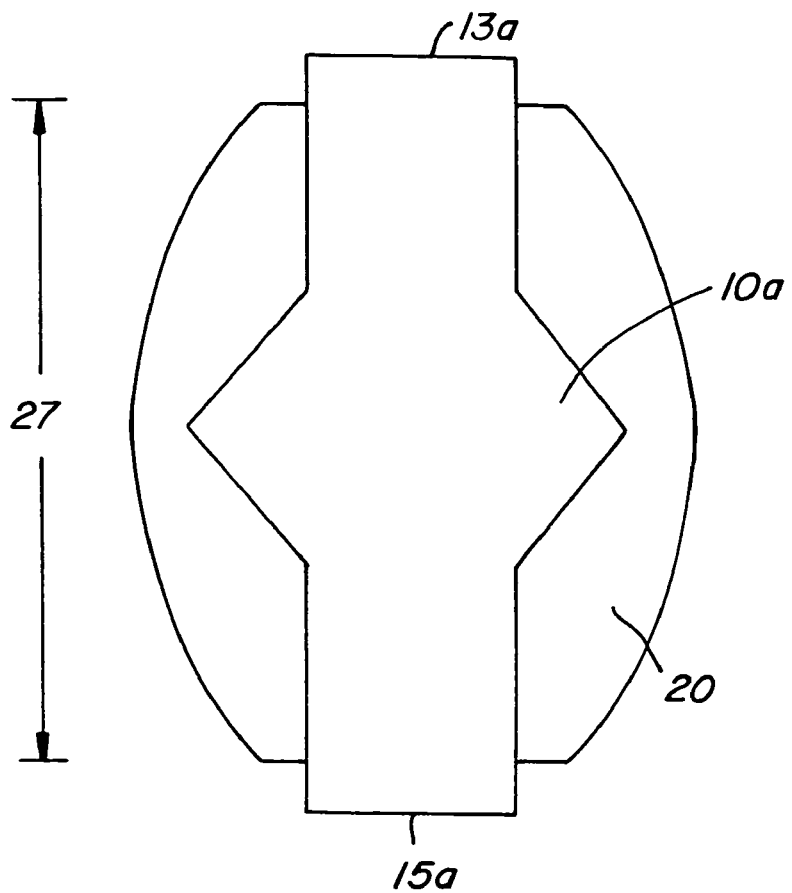
FIG. 25 is a view corresponding to FIG. 24, after the bone block has been rotated into an anchored position between two adjacent vertebrae.

In an alternate aspect of the present invention, the need for push rod 30 is eliminated by dimensioning the bone block as seen in FIGS. 24 and 25. Specifically, in this aspect of the invention, vertebral contact surfaces 13b and 15b of bone block 10b extend slightly beyond major dimension 27 of inserter 20. As shown in FIG. 25, when bone block 10b is rotated into position, vertebral contact surfaces 13b and 15b will tend to anchor against vertebrae 50 and 52 as the vertebrae rest thereon, as shown. As such, bone block 10b will be firmly held in an anchored position such that inserter 20 can be slidably removed without having to hold bone block 10b in a fixed position with a push rod which removing inserter 20.

Figure 26:
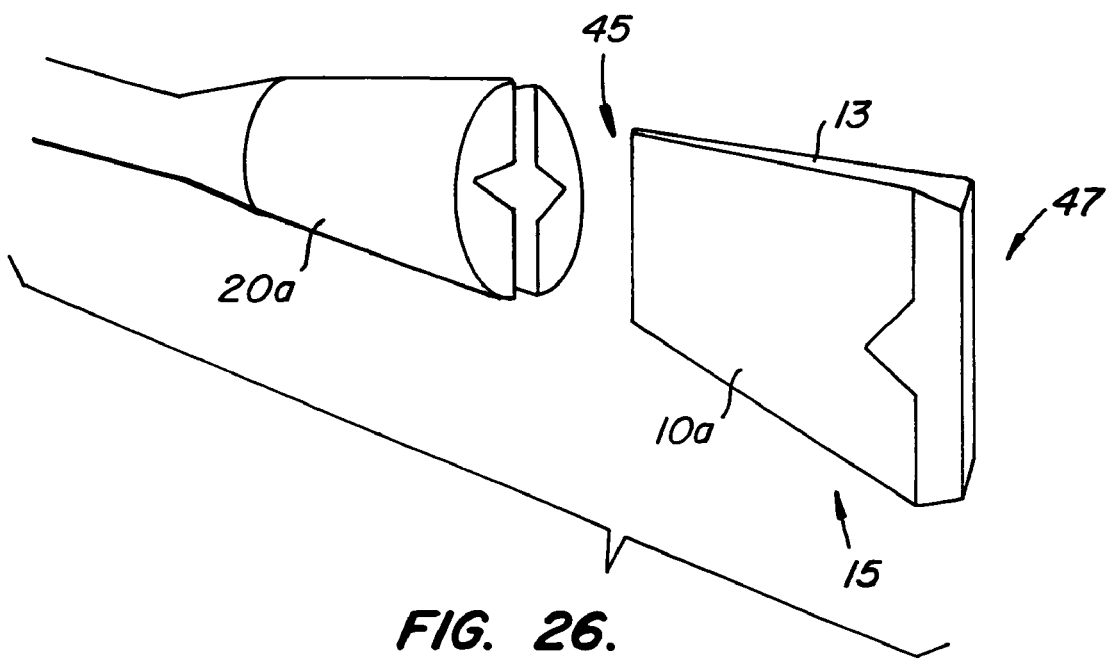
FIG. 26 is an exploded view of a tapered bone block and a tapered inserter.

Optionally, as is seen in FIG. 26, vertebral support surfaces 13 and 15 of bone block 10c may be angled with respect to one another to taper from a short posterior end 45 to a tall anterior end 47. The tapering of bone block 20 from a tall anterior end 47 to a short posterior end 45 supports the adjacent vertebrae at a required lordosis angle when the inserts are positioned therebetween. A suitable tapered inserter 20a is also shown.

Figure 27:
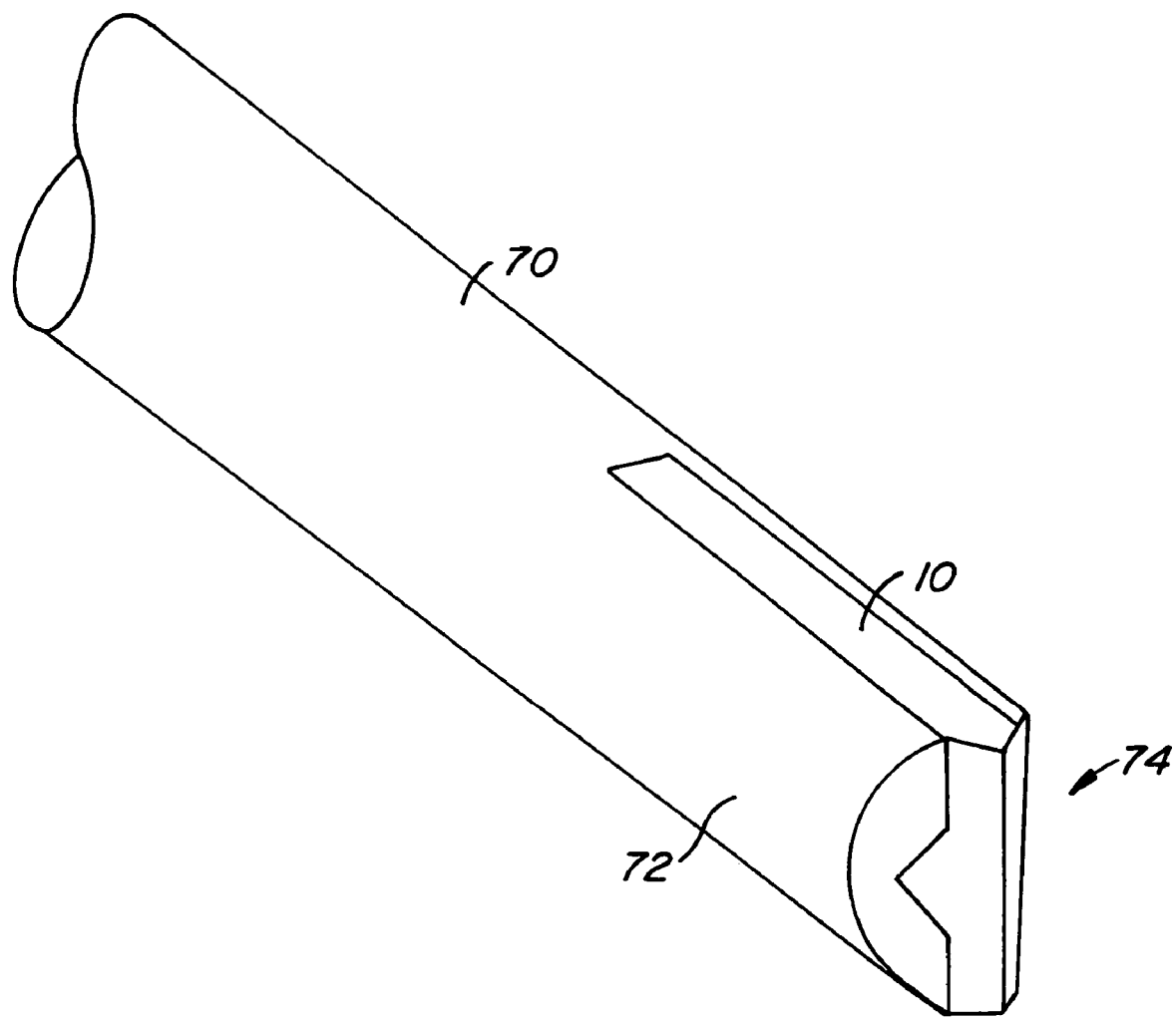
FIG. 27 is a perspective view of a cannula dimensioned to support a bone block at its distal end.

As seen in FIG. 27, a cannula 70 may be dimensioned to have convexly curved camming surfaces 72 and 74 at its distal end. Cannula 70 is dimensioned similar to inserter 20 to support bone block 10 therein. In this aspect of the invention, however, the need for a separate cannula and inserter is overcome as the cannula itself acts as the bone block inserter, with the cannula itself being rotated 90° to cam apart the adjacent vertebrae.

The present invention also provides systems for introducing two bone blocks into the patient's intervertebral space, and optionally interlocking these bone blocks together. Preferably, the two bone blocks are oriented at an angle from 70° to 135° to one another. Most preferably, this angle is about 90°. Both the first and the second bone blocks are each preferably positioned between the adjacent vertebrae using the above described method of inserting a single bone block. In this case, the first bone block inserter will provide most of the camming action to separate the adjacent vertebrae, with the second bone block inserter being received into an already distracted intervertebral space.

Figure 16:
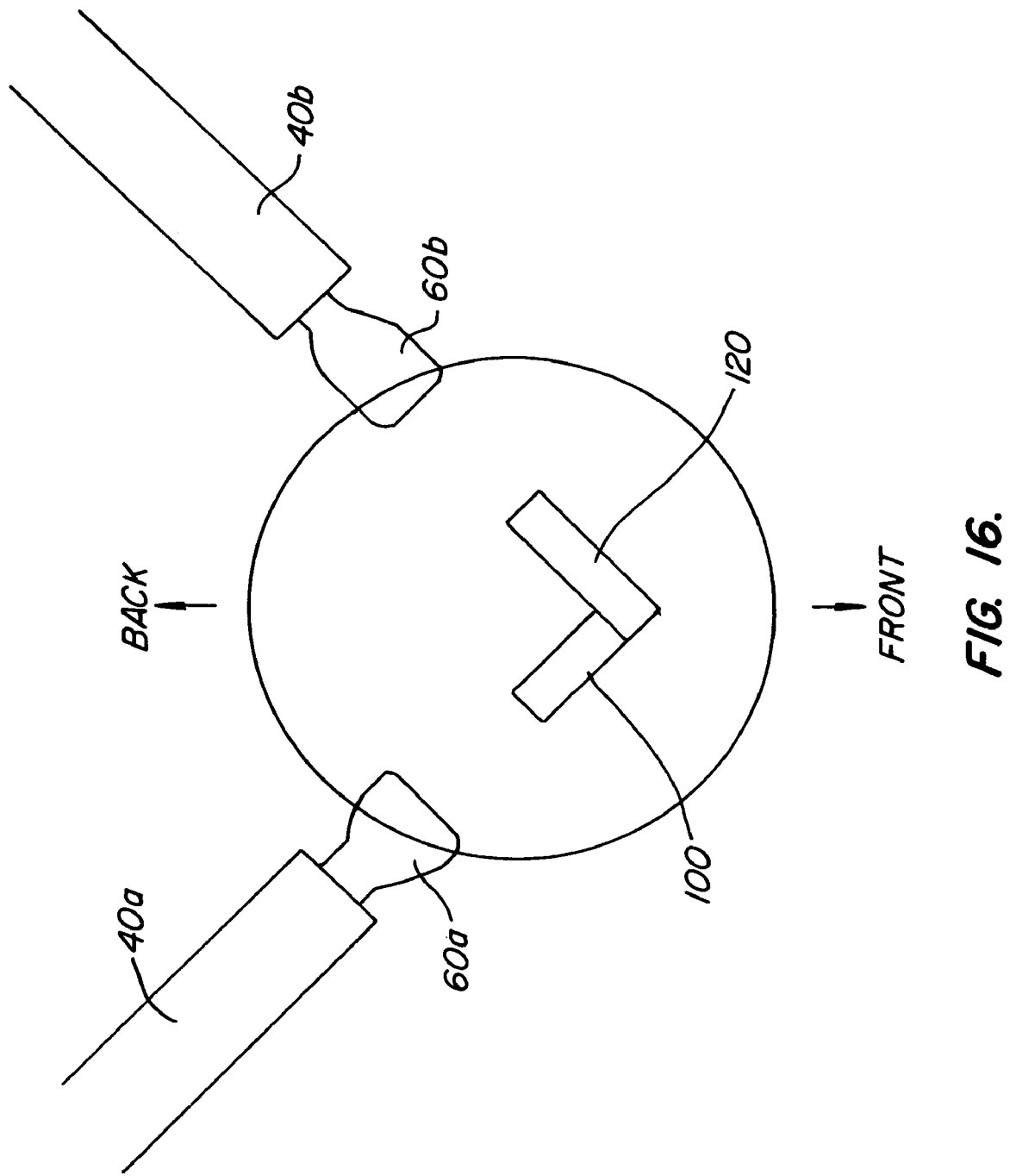
FIG. 16 is a top perspective view of two interlocking bone blocks, showing two posterolateral cannulae for introducing the two interlocking bone blocks into the patient's intervertebral space.

Referring to FIG. 16, cannula 40a and 40b may be positioned generally perpendicular to one another in posterolateral approaches as shown. Cannula 40a and 40b are preferably percutaneously introduced into the patient's back in a minimally invasive surgical procedure.

Inserter 60a is received in cannula 40a and inserter 60b is received in cannula 40b, as shown. Inserter 60a positions bone block 100 and inserter 60b positions bone block 120 such that bone blocks 100 and 120 are generally perpendicular to one another, as shown. FIG. 16 shows the positioning of inserters 60a and 60b after the inserters have been partially withdrawn, leaving bone blocks 100 and 120 interlocked together in the patient's intervertebral space. It is to be understood, however, that the present invention also includes positioning the first and second bone blocks in the intervertebral space without interlocking the bone blocks together and without positioning the bone blocks at an angle to one another.

Figure 12:
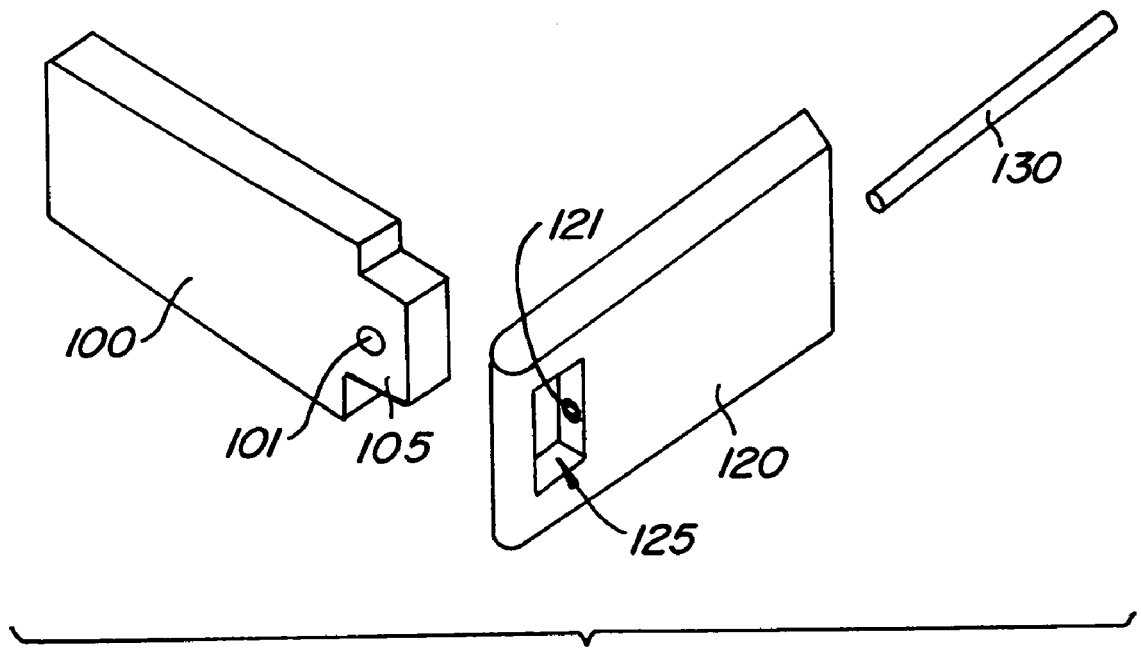
FIG. 12 is an exploded perspective view showing the interlocking of first and second bone blocks with a fastening pin.
Figure 13:
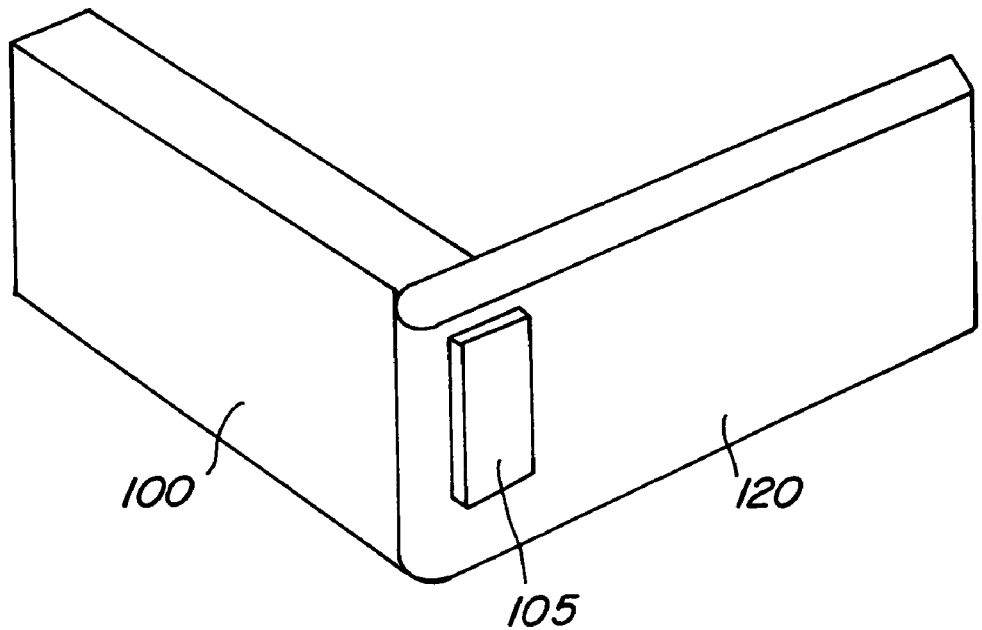
FIG. 13 is a view corresponding to FIG. 12, but with the first and second bone blocks fastened together.

Being disposed generally perpendicular to one another, inserts 100 and 120 offer both increased back-to-front and side-to-side stability between the patient's adjacent vertebrae. An advantage of this enhanced stability is that bone blocks 100 and 120 can each be made relatively tall and narrow as is shown by the shape of bone blocks 100 and 110 in FIGS. 12 and 13. Such tall and narrow bone blocks have the advantage of requiring substantially less donor tissue in their fabricating than existing bone blocks.

Figure 2:
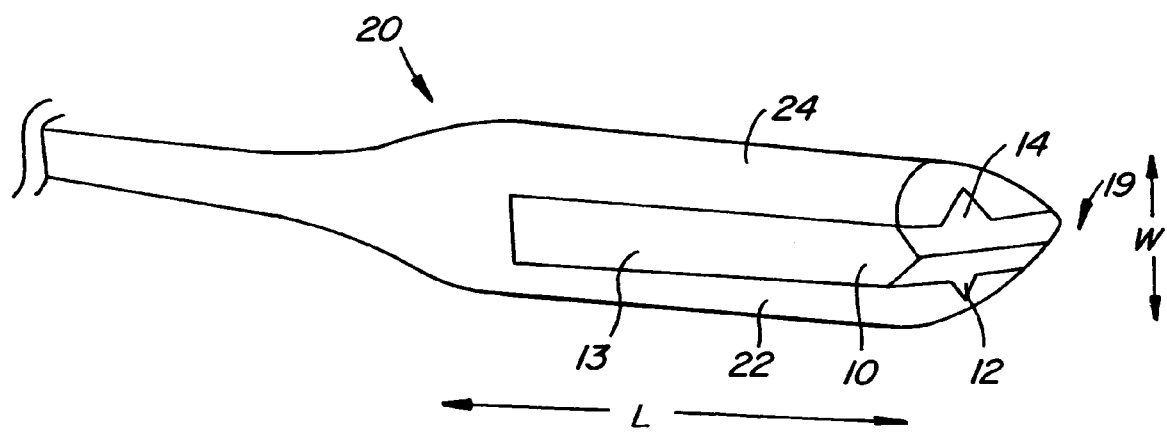
FIG. 2 is an alternate perspective view of the inserter and bone block of FIG. 1.

In a preferred aspect, bone block 10 is dimensioned to be 12 to 24 mm in length, (ie: the L dimension in FIGS. 1 and 2), 6-16 mm in height, (ie: the H dimension in FIGS. 1 and 2), and 4-8 mm in width, (ie: the W dimension in FIGS. 1 and 2). Referring to FIGS. 6 and 7, vertebral contact surfaces 13 and 15 are therefore about 12-24 mm by 4-8 mm in area.

As seen in FIGS. 6 and 7, bone block 10 and 10a are each preferably dimensioned such that the opposite vertebral contact surfaces 13 and 15 each have a width W1 which is about 20% to 60% and most preferably 30% of H1 as shown, (H1 being the height of the opposite sides spanning between the opposite vertebral contact surfaces).

Figure 14:
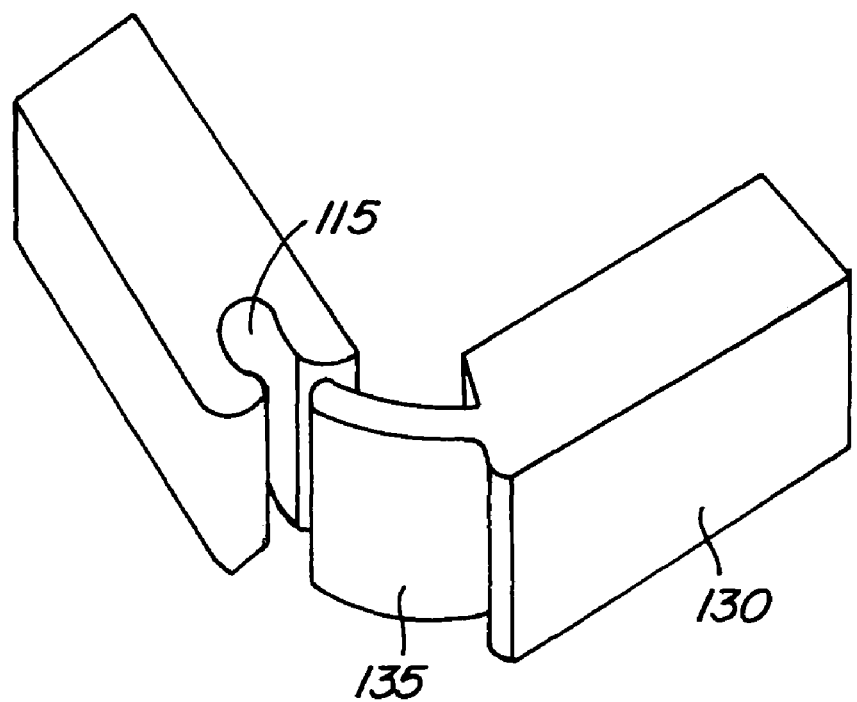
FIG. 14 is an alternate design of first and second interlocking bone blocks.
Figure 15:
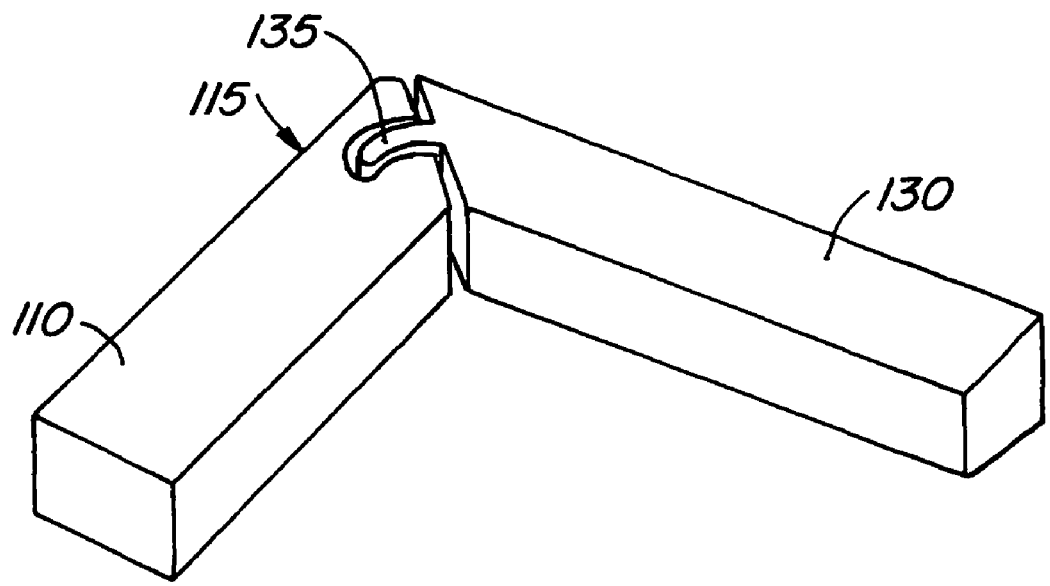
FIG. 15 is a bottom view corresponding to FIG. 14 but with the first and second bone blocks interlocked together.

Bone blocks 100 and 120 may be interlocked together as desired using a variety of techniques. For example, referring to FIGS. 12 and 13, bone blocks 100 and 120 can be interlocked by way of protrusion 105 on bone block 100 being received into an aperture 125 in bone block 120. An optional fastening pin 130 may also be used to interlock bone blocks 100 and 120 together. In this aspect of the invention, fastening pin 130 is received through a central bore 121 in bone block and passes through bore 101 in protrusion 105, thereby fixedly interlocking the bone blocks together. In an alternate interlocking bone block configuration shown in FIGS. 14 and 15, bone blocks 110 and 130 are interlocked together by way of a groove 115 on bone block 110 receiving a notch 135 projecting from bone block 130 therein as shown.

Figure 23:
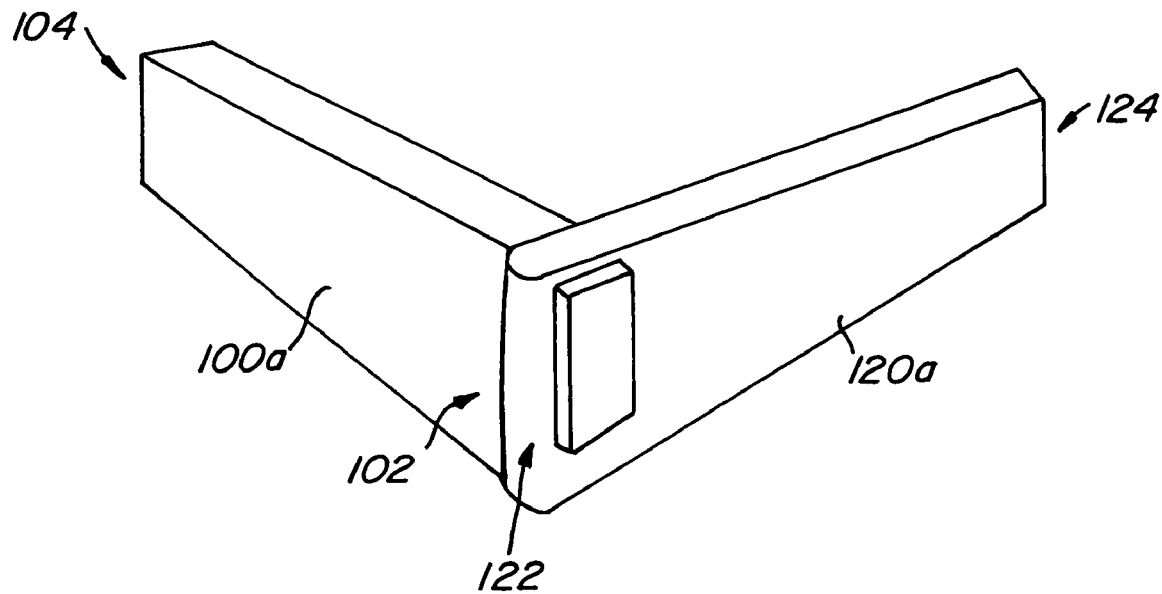
FIG. 23 is an illustration of interlocking bone blocks which are tapered to compensate for the patient's lordotic angle.

In another aspect of the invention, the interlocked bone blocks (and the inserter) are tapered to compensate for the patient's lordotic angle. Specifically, FIG. 23 illustrates bone blocks 100a and 120a which are angled to display such tapering. Specifically, bone blocks 100a and 120a are shorter at their non-interlocked ends 104 and 124 than at their interlocked ends 102 and 122, as shown.

Figure 28:
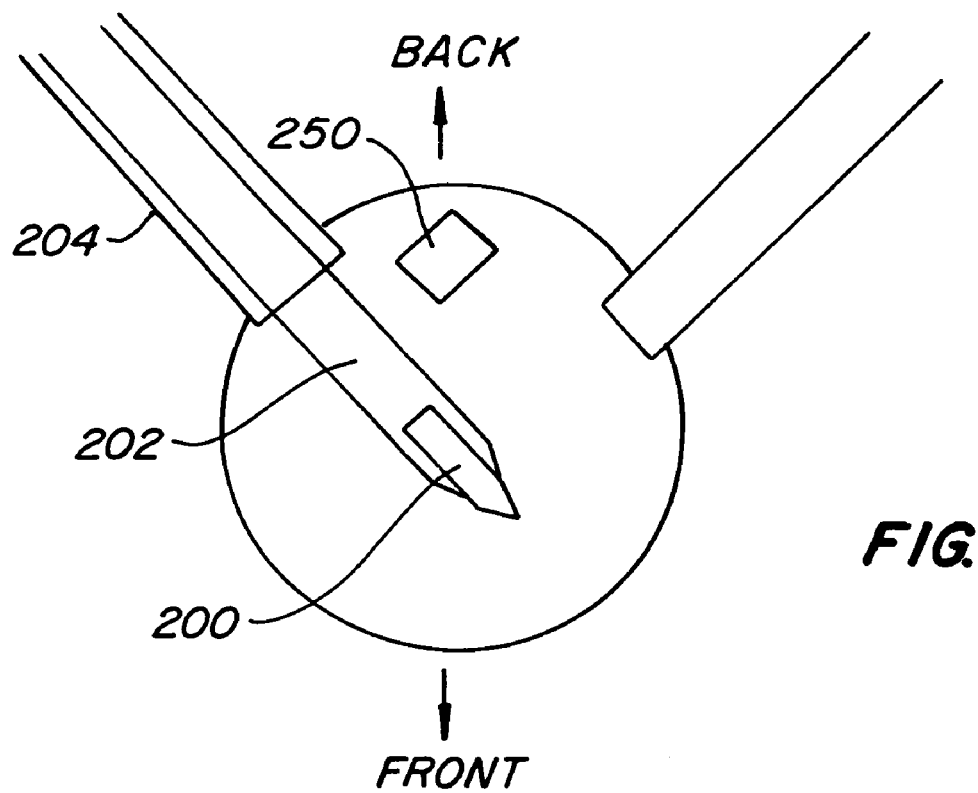
FIG. 28 shows a first step in inserting a quartet of bone blocks.
Figure 29:
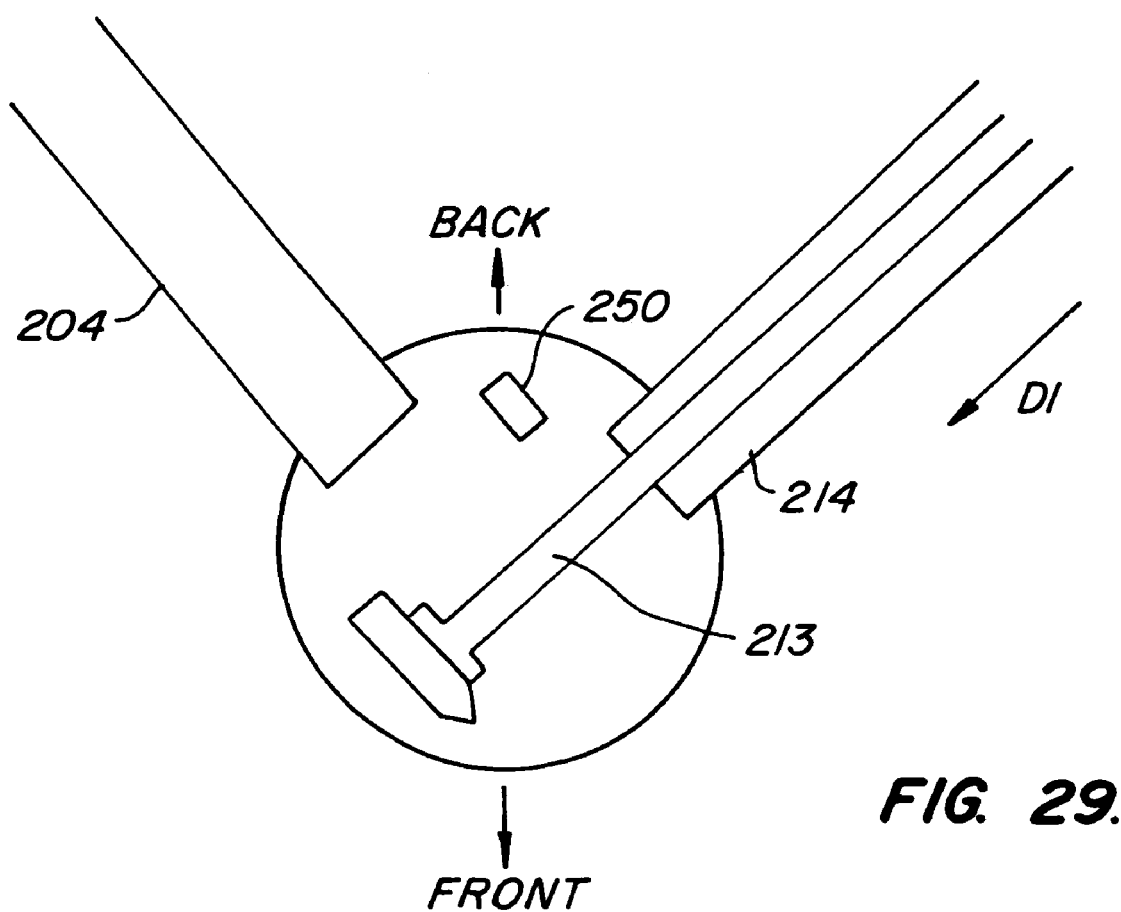
FIG. 29 shows a second step in inserting a quartet of bone blocks.
Figure 30:
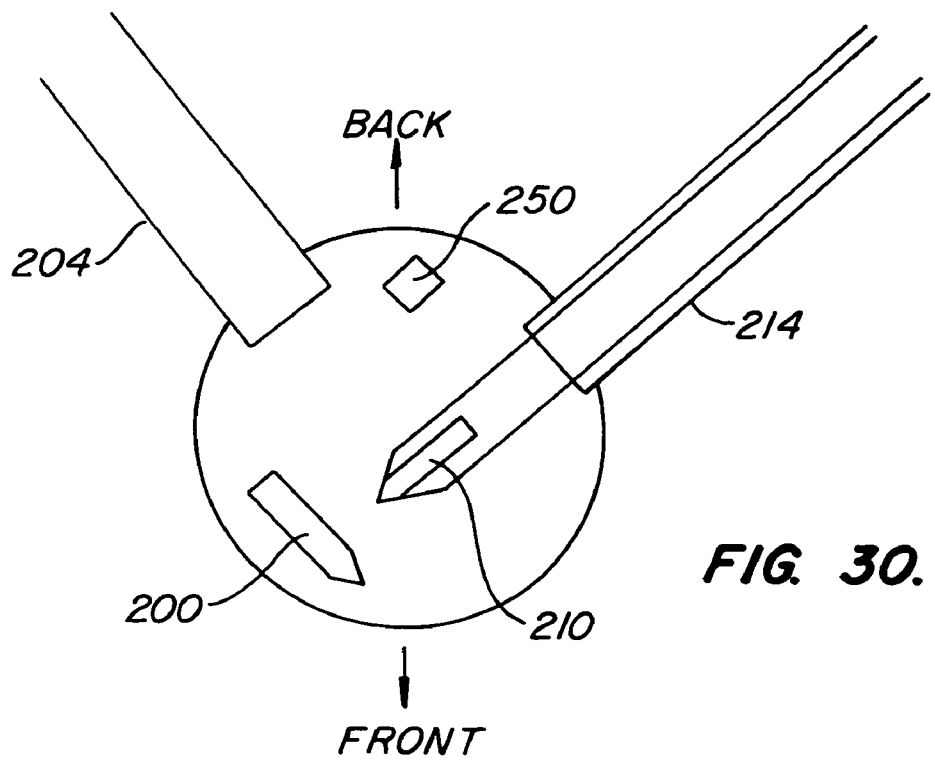
FIG. 30 shows a third step in inserting a quartet of bone blocks.
Figure 31:
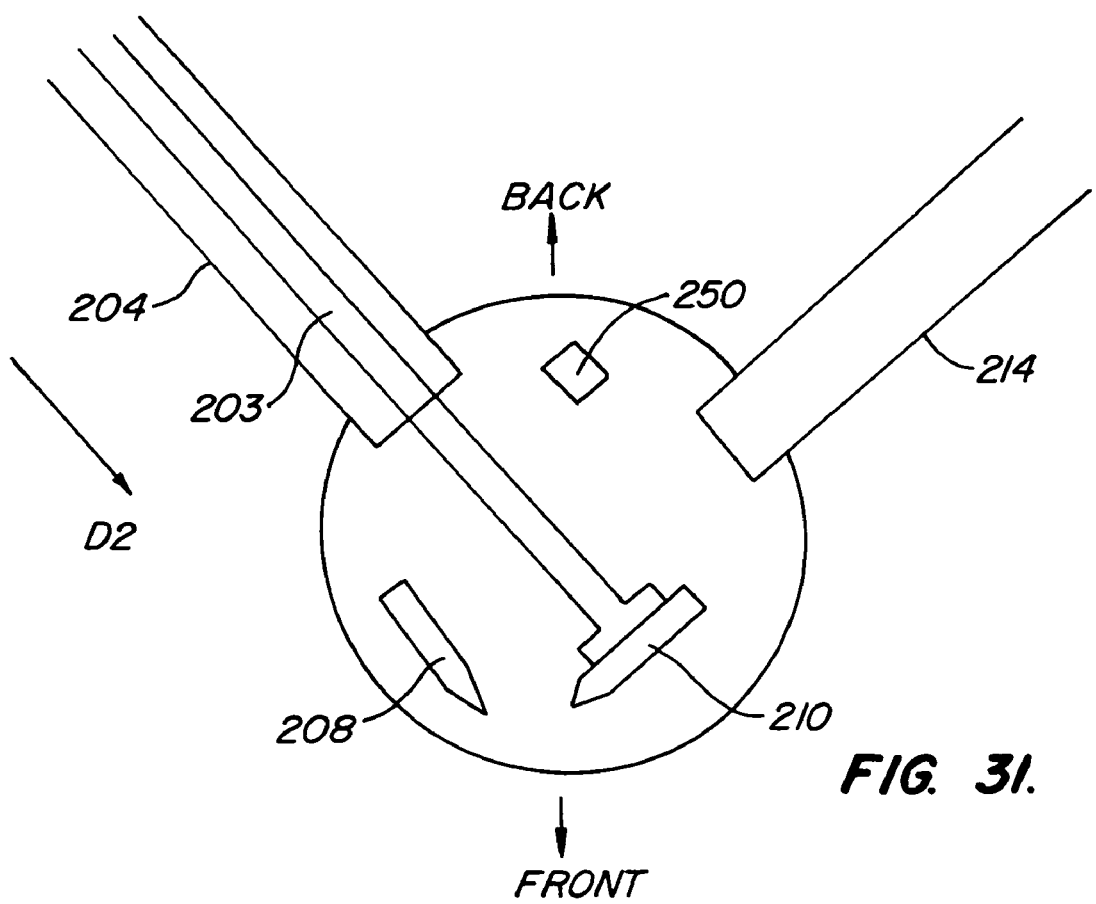
FIG. 31 shows a fourth step in inserting a quartet of bone blocks.
Figure 32:
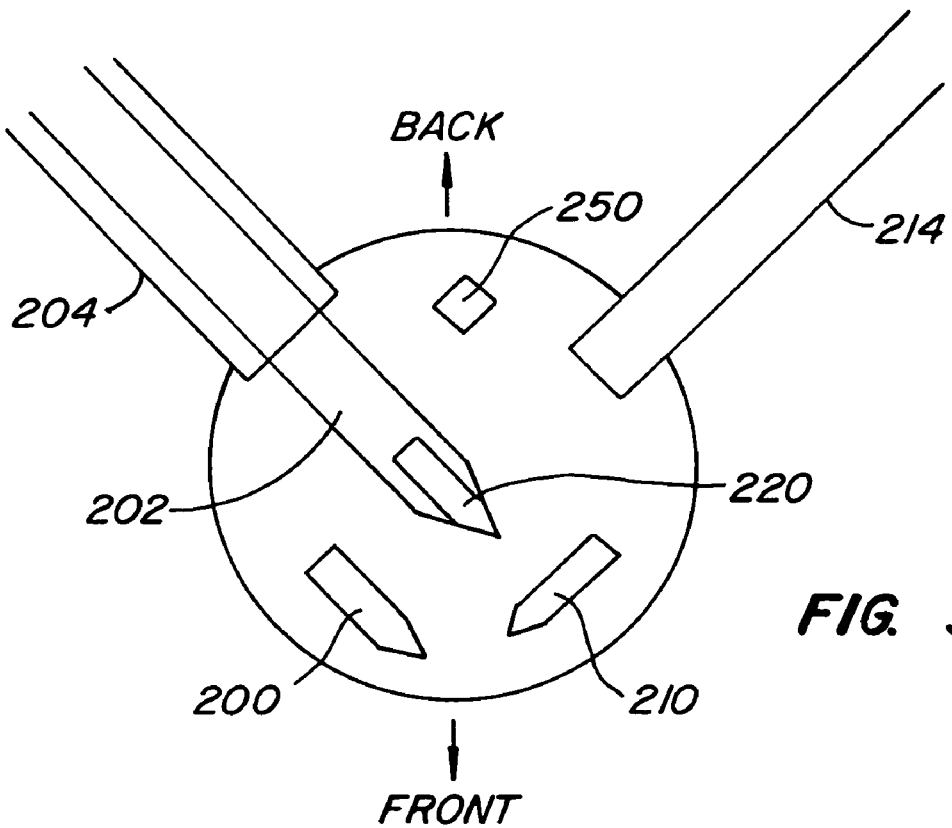
FIG. 32 shows a fifth step in inserting a quartet of bone blocks.
Figure 33:
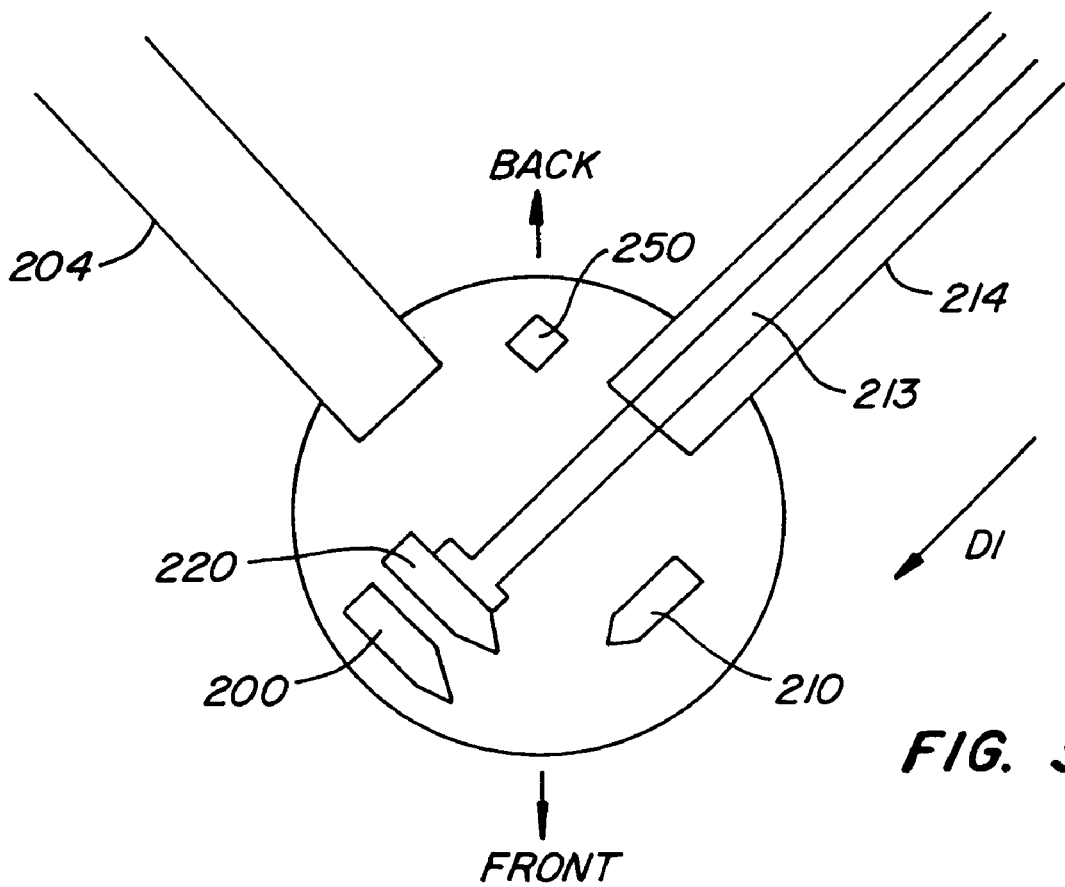
FIG. 33 shows a sixth step in inserting a quartet of bone blocks.
Figure 34:
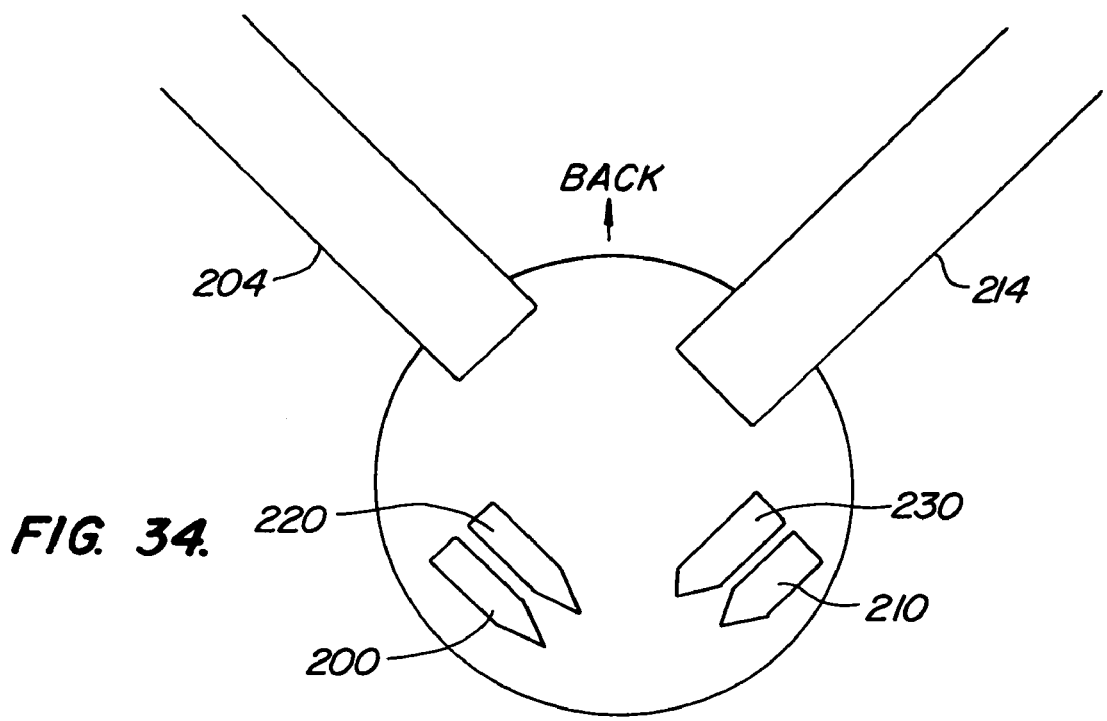
FIG. 34 shows a seventh step in inserting a quartet of bone blocks.

Increasing numbers of bone blocks will provide an increased surface area for support between the adjacent vertebrae. Accordingly, the present invention also encompasses inserting more than 2 bone blocks into the patient's intervertebral space, as follows. FIGS. 28 to 34 show sequential steps in inserting a quartet of bone blocks 200, 210, 220 and 230, as follows. In FIG. 28, a first bone block 200 is inserted into a patient's intervertebral space and rotated into position by inserter 202 received through cannula 204. Subsequently, as shown in FIG. 29, inserter 202 is removed and push rod 213 is inserted through cannula 214, moving bone bock 200 in direction D1. Subsequently, as shown in FIG. 30, a second block 210 is inserted into a patient's intervertebral space and rotated into position by inserter 212 received through cannula 214. Subsequently, as shown in FIG. 31, inserter 212 is removed and push rod 203 is inserted through cannula 204, moving bone bock 210 in direction D2. Subsequently, as shown in FIG. 31, a third block 220 is inserted into a patient's intervertebral space and rotated into position by inserter 202 received through cannula 204. Subsequently, as shown in FIG. 33, inserter 202 is removed and push rod 213 is inserted through cannula 214, moving bone bock 220 in direction D1. Finally, as shown in FIG. 34, a fourth block 230 is positioned in the patient's intervertebral space using the above described methods. An optional temporary distractor 250 may be positioned in the patient's intervertebral space during the above described procedure to increase the access for sliding bone blocks 200, 210, 220 and 230 into position.

The illustrations of FIGS. 28 to 34 showing a quartet of bone blocks 200, 210, 220, and 230 inserted into the patient's intervertebral space is exemplary of the number of bone blocks which may be inserted into the intervertebral space. As such, more than four bone blocks, (for example 6, 8, 10 or more), may instead be used. In addition, odd numbers of bone blocks may be used as well, such as when dealing with non-symmetries in the patient's intervertebral space.

Figure 35:
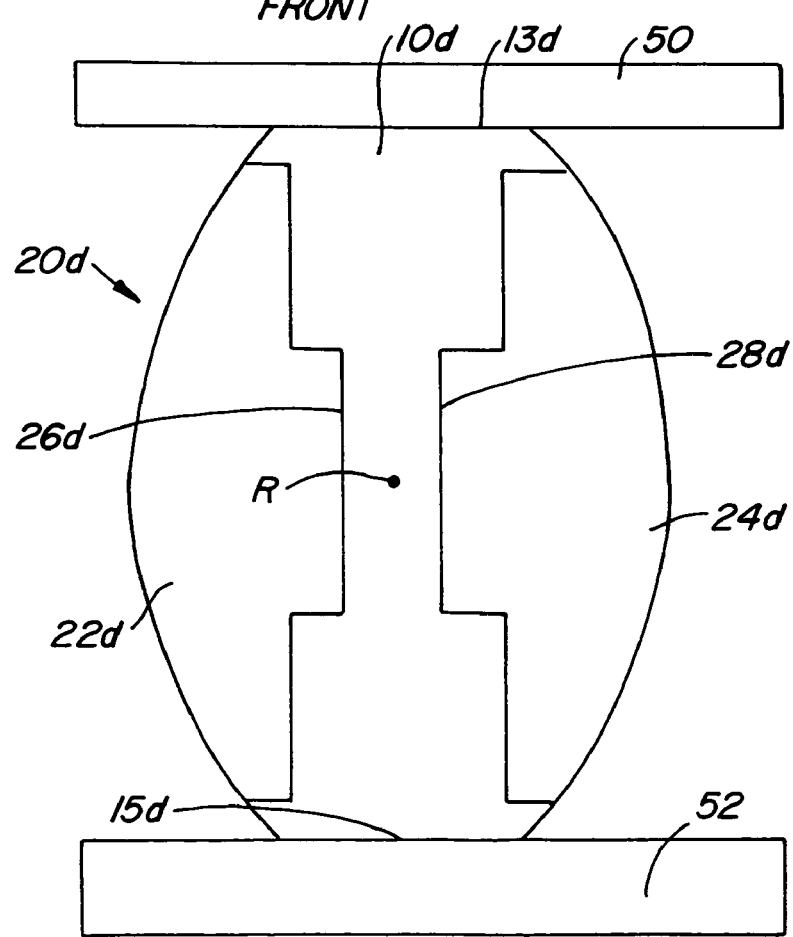
FIG. 35 shows an end view of an alternate bone block.

As can be seen in FIG. 35, an alternate bone block 10d can be fabricated into an I-beam shape. An advantage of bone block 10d is its large vertebral support surfaces 13d and 15d. As seen in this design, (and as could be optionally included on other designs herein), grooves 26d and 28d on inserter 20d project inwardly.

Figure 17:
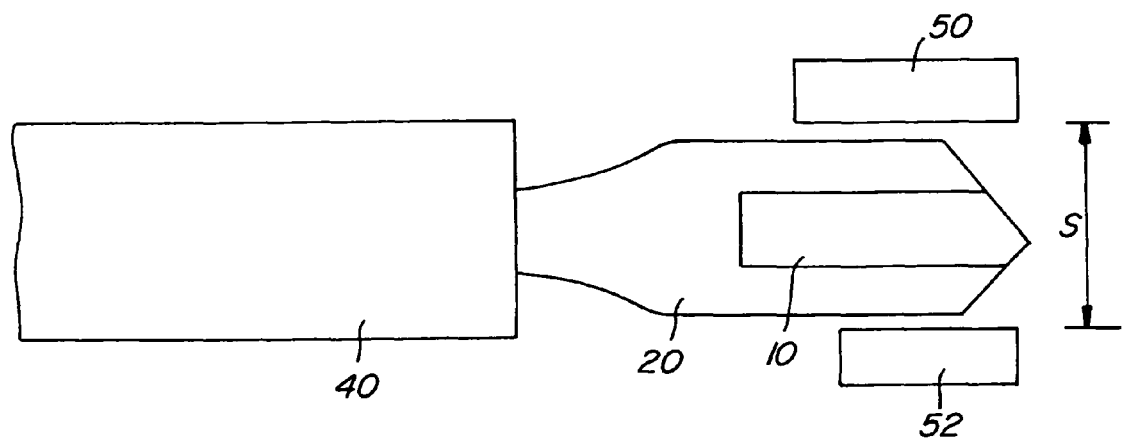
FIG. 17 is a side view of the inserter as received in an oval or racetrack shaped cannula, showing the orientation of the inserter when initially received in the intervertebral space.
Figure 19:
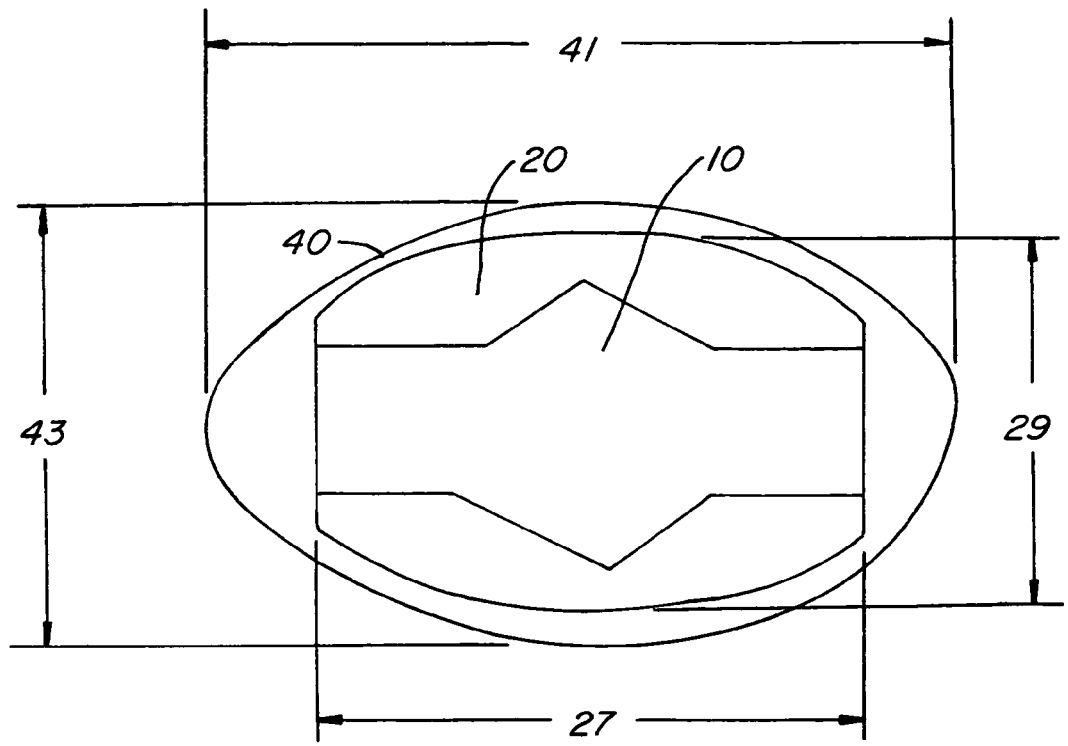
FIG. 19 is an end view corresponding to FIG. 17.

In various aspects of the invention, a bone block inserter is preferably received in a cannula which has been percutaneously introduced into the patient in a posterolateral approach. Referring to FIG. 17, inserter 20 is preferably advanced through cannula 40 into the patient's intervertebral space. As can be seen in FIG. 19, cannula 40 preferably has an oval shape or a racetrack shape wherein the shape of the cannula is defined by an ellipse having a major dimension 41 and a minor dimension 43.

Figure 20:
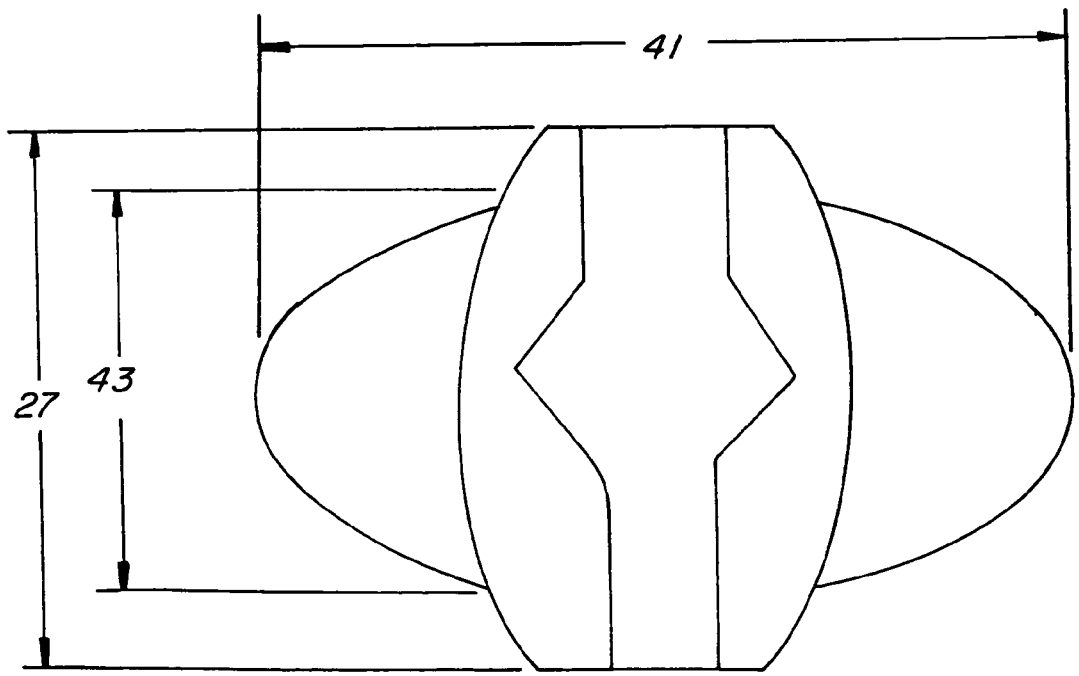
FIG. 20 is an end view corresponding to FIG. 18.

As can be seen in FIGS. 6, 7, 19 and 20, inserter 20 has a cross-section which is defined by a major dimension 27 and a minor dimension 29. As can be seen in FIG. 19, inserter 20 is dimensioned to pass through cannula 40 when major dimension 27 and major dimension 41 are parallel. Rotation of inserter 20 by 90° during placement of bone block 10 between adjacent vertebrae 50 and 52 will cause inserter 20 to be oriented with its major dimension 27 (see FIGS. 6 and 7), oriented generally perpendicular to major dimension 41 of cannula 40 as shown in FIGS. 18 and 20.

Figure 18:
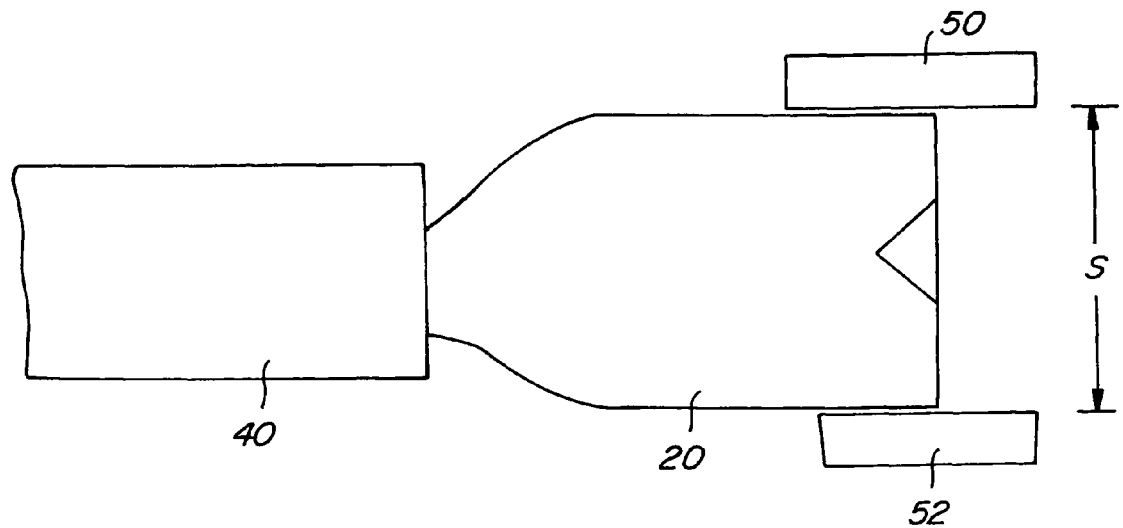
FIG. 18 is a side view of the inserter as received in an oval or racetrack shaped cannula, showing the orientation of the inserter after it has been rotated by 90°.
Figure 21:
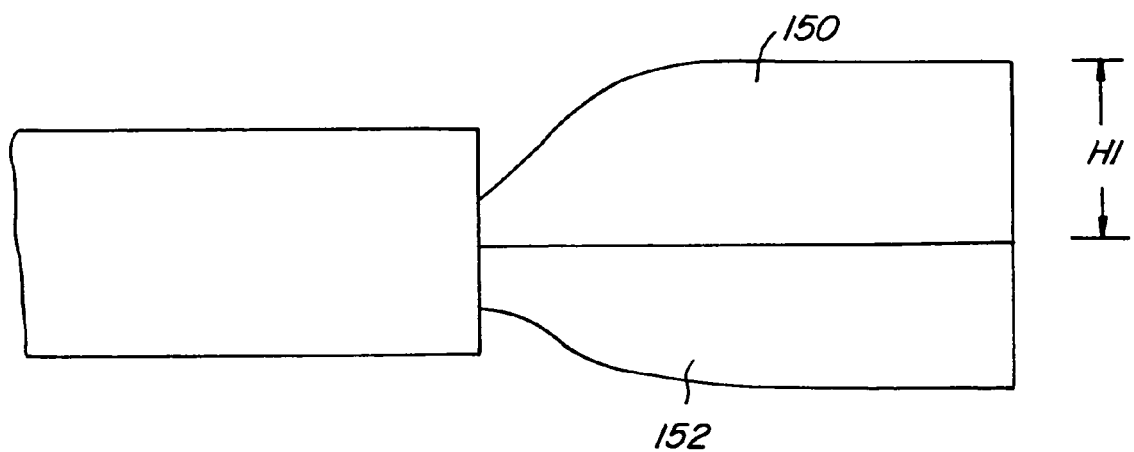
FIG. 21 is view corresponding to FIG. 18, showing the sectioning of the inserter for removal through the catheter.

Removal of inserter 20 through cannula 40 when inserter 20 is oriented as shown in FIGS. 18 and 20 can be accomplished as follows. Referring to FIG. 21, inserter 20 can be fabricated such that it can be broken apart into at least two longitudinally extending sections 150 and 152. Preferably, sections 150 and 152 will comprise opposite halves of the inserter, as shown.

Figure 22:
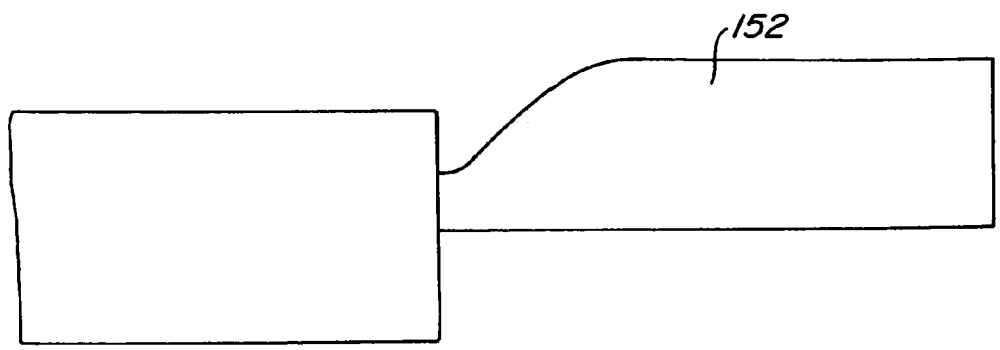
FIG. 22 is a view corresponding to FIG. 21, but with one section of the inserter removed.

Each of longitudinally extending sections 150 and 152 will have a height H2, (wherein H2 is half the distance of H1), which is less than minor dimension 43 of cannula 40. Accordingly, sections 150 and 152 can be separately withdrawn through cannula 40 one at a time while inserter 20 is positioned at shown in FIGS. 18 and 20. FIG. 22 shows inserter 20 after section 152 has been removed.

Figure 37:
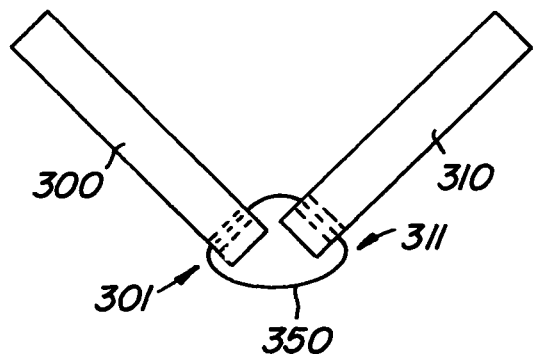
FIG. 37 shows a pair of bone blocks angled to one another with ends of the bone blocks sutured together.
Figure 38:
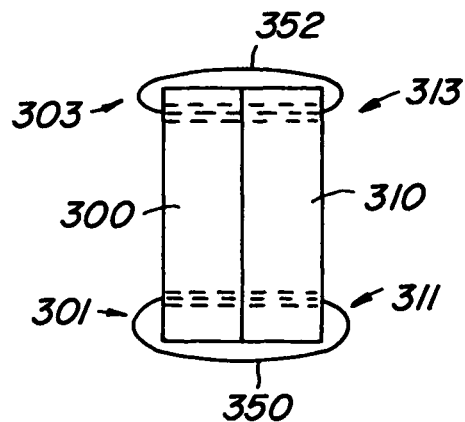
FIG. 38 shows a pair of parallel bone blocks sutured together.

In another aspect of the invention, FIG. 37 shows a pair of bone blocks 300 and 310 angled to one another with ends of the inserts sutured together by suture 350 passing through holes 301 and 311 in bone blocks 300 and 310, respectively. FIG. 38 shows a pair of parallel bone blocks 300 and 310 sutured together at both ends by suture 350 passing through holes 301 and 311 in bone blocks 300 and 310 and suture 352 passing through holes 303 and 313 in bone blocks 300 and 310.

Figure 36:
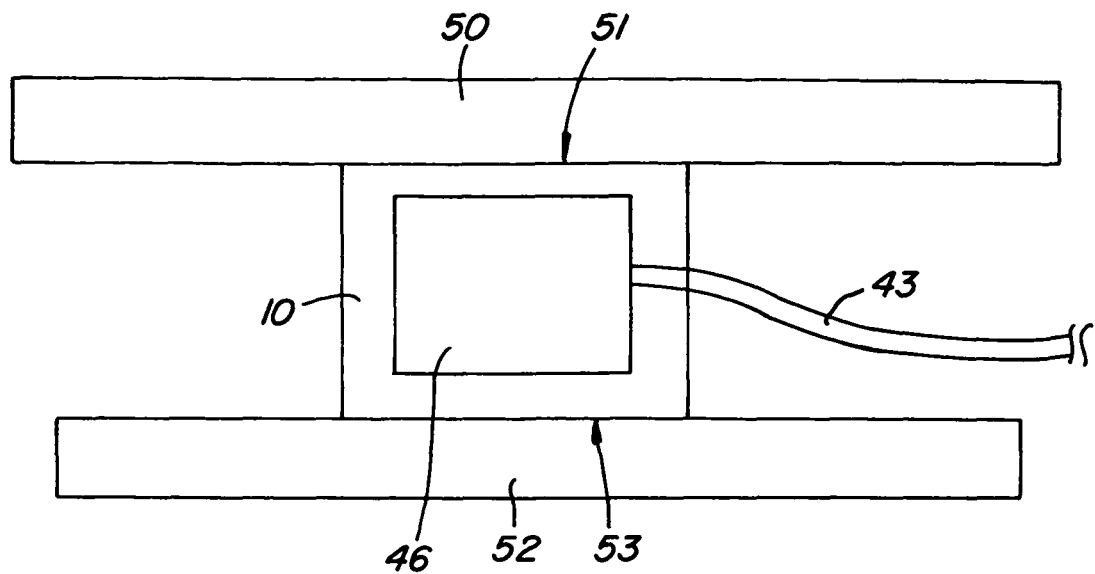
FIG. 36 is a schematic illustration of a bone block with an electronic transducer therein.

In yet another aspect of the present invention, as shown schematically in FIG. 36, bone block 10 has an electronic transducer 46 fabricated therein.

Bone block 10 has at least one surface 51 which will be loaded by repetitive spinal loading thereagainst. As shown in FIG. 36, bone block 10 may simultaneously be placed adjacent to vertebrae 50 and 52 with surfaces 51 and 53 being loaded by bone motion. In one preferred aspect, loading of transducer 46 will be provided by normal spinal loading.

Transducer 46 operates to generate an electric current when it is subjected to stress loading. Transducer 46 can comprise a piezoelectric crystal which generates an electric current when bone block 20 is subjected to normal repetitive loading through the patient's spine. Alternatively, transducer 46 can comprise a battery which continuously generates an electric current. A wire 43 operates to deliver the generated current to a preferred bone, bone graft or other area for bone formation. The body of bone dowel 10 may itself act as a ground for wire 43. Transducer 46 operates to produce electrical voltage and current of a type and in an amount sufficient to induce osteogenesis in the bone. Specifically, a preferred current is in the range of 1 to 10 microamps/cm$^2$, and most at least about 2.5 microamps/cm$^2$.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A method for inserting a spinal implant into an intervertebral space, comprising:
    coupling a spinal implant with an inserter, the spinal implant having first and second vertebral contact surfaces and first and second sides spanning between the first and second vertebral contact surfaces, wherein the first and second sides include engagement features to facilitate engagement of the spinal implant with an inserter, at least a portion of said first and second sides comprising curved camming surfaces;
    advancing the inserter into the intervertebral space;
    rotating the inserter by 90°, thereby causing the curved camming surfaces of the implant to contact the vertebrae and separate the adjacent vertebrae by camming action; and
    removing the inserter from the intervertebral space.

2. The method of claim 1, wherein the engagement features comprise lateral protrusions which extend longitudinally along the length of the spinal implant.

3. The method of claim 1, wherein the spinal implant has an angled front end.

4. The method of claim 1, wherein the spinal implant tapers between longitudinally spaced apart ends, thereby compensating for a lordotic angle between adjacent vertebrae in the patient's intervertebral space.

5. The method of claim 1, wherein the spinal implant includes an electrical transducer, the transducer adapted to produce electrical current of a type and in an amount sufficient to induce osteogenesis in adjacent vertebrae as the result of relative spinal loading of the spinal implant.

6. The method of claim 1, wherein the implant is made of bone.

7. The method of claim 1, wherein rotating the inserter thereby separating the adjacent vertebrae by camming action comprises:

engaging convexly curved camming surfaces on the inserter against the adjacent vertebrae.

8. The method of claim 1, wherein advancing the inserter into the intervertebral space comprises:

advancing the inserter through a cannula which has been percutaneously introduced into the patient.

9. The method of claim 8, wherein the cannula is introduced in a posterolateral approach.

10. The method of claim 8, wherein the cannula has an oval or racetrack-shaped cross section, the cross section being defined by an ellipse having a major dimension and a minor dimension.

11. The method of claim 10, wherein the cannula is disposed with the major dimension of the ellipse parallel to the adjacent vertebrae, and the inserter has a cross section defined by a major dimension and a minor dimension, wherein rotation of the inserter causes the major dimension of the inserter to be disposed perpendicular to the adjacent vertebrae.

12. The method of claim 1, wherein the inserter has a central longitudinally extending axis, and wherein rotating the inserter comprises:

rotating the inserter about a central longitudinal axis passing therethrough.

13. The method of claim 1, wherein removing the inserter comprises:

rotating the spinal implant to an anchored position such that the vertebral support surfaces on the spinal implant engage the adjacent vertebrae, holding the spinal implant in position and slidably withdrawing the inserter from the spinal implant.

14. A method for introducing a spinal implant into the intervertebral space of a patient, comprising:

coupling a spinal implant with an inserter to form an assembly, the assembly configured for rotation in multiple directions, the spinal implant having first and second vertebral contact surfaces and first and second sides spanning between the first and second vertebral contact surfaces, wherein the first and second sides include engagement features to facilitate engagement of the spinal implant with an inserter, at least a portion of said first and second sides comprising curved camming surfaces;

advancing the assembly into the intervertebral space;

rotating the assembly by 90°, thereby causing the curved camming surfaces of the implant to contact the vertebrae and separate the adjacent vertebrae by camming action; and removing the inserter from the intervertebral space.

15. The method of claim 14, wherein the engagement features comprise lateral protrusions which extend longitudinally along the length of the spinal implant.

16. The method of claim 14, wherein the spinal implant has an angled front end.

17. The method of claim 14, wherein the spinal implant tapers between longitudinally spaced apart ends, thereby compensating for a lordotic angle between adjacent vertebrae in the patient's intervertebral space.

18. The method of claim 14, wherein the spinal implant includes an electrical transducer, the transducer adapted to produce electrical current of a type and in an amount sufficient to induce osteogenesis in adjacent vertebrae as the result of relative spinal loading of the spinal implant.

19. The method of claim 14, wherein the implant is made of bone.

* * * * *